(12) United States Patent
Bailey et al.

(10) Patent No.: US 9,561,010 B2
(45) Date of Patent: *Feb. 7, 2017

(54) ANATOMICAL IMAGING SYSTEM WITH CENTIPEDE SCANNING DRIVE, BOTTOM NOTCH TO ACCOMMODATE BASE OF PATIENT SUPPORT, AND MOTORIZED DRIVE FOR TRANSPORTING THE SYSTEM BETWEEN SCANNING LOCATIONS

(71) Applicant: NeuroLogica Corp., Danvers, MA (US)

(72) Inventors: Eric M. Bailey, North Hampton, NH (US); Andrew P. Tybinkowski, Boxford, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/541,247

(22) Filed: Nov. 14, 2014

(65) Prior Publication Data

US 2015/0196263 A1   Jul. 16, 2015

Related U.S. Application Data

(63) Continuation of application No. 13/304,006, filed on Nov. 23, 2011, now Pat. No. 8,888,364, which is a (Continued)

(51) Int. Cl.
*A61B 6/00*   (2006.01)
*A61B 6/03*   (2006.01)
(Continued)

(52) U.S. Cl.
CPC .............. *A61B 6/461* (2013.01); *A61B 6/035* (2013.01); *A61B 6/0457* (2013.01); *A61B 6/4405* (2013.01); *A61B 6/501* (2013.01); *A61B 6/508* (2013.01); *G01N 23/046* (2013.01); *A61B 5/055* (2013.01); *A61B 6/037* (2013.01); *A61B 6/102* (2013.01); *A61B 6/4435* (2013.01); *G01N 2223/419* (2013.01); *G01N 2223/612* (2013.01)

(58) Field of Classification Search
CPC ....... A61B 6/461; A61B 6/035; A61B 6/4405; G01N 23/04
USPC ........................................ 378/193–198, 4–20
See application file for complete search history.

(56) References Cited

U.S. PATENT DOCUMENTS 2,765,860 A   10/1956   Church
3,603,975 A    9/1971   Gordon
(Continued)

FOREIGN PATENT DOCUMENTS

CN          1037450      11/1989
JP       HEI 11-164829    6/1999
(Continued)

*Primary Examiner* — Courtney Thomas
(74) *Attorney, Agent, or Firm* — Pandiscio & Pandiscio

(57) ABSTRACT

An imaging system including a scanner for scanning an object and creating an image of the same; and a transport mechanism mounted to the scanner for moving the scanner, wherein the transport mechanism includes a gross movement mechanism for transporting the scanner between scanning locations; and a fine movement mechanism for moving the scanner precisely, relative to the object being scanned, during scanning of the object; wherein the gross movement mechanism comprises at least one motorized wheel.

28 Claims, 27 Drawing Sheets

BodyTom™ CT Machine (Front)

Related U.S. Application Data continuation-in-part of application No. 12/655,360, filed on Dec. 29, 2009, now Pat. No. 8,251,584, which is a continuation of application No. 11/706,133, filed on Feb. 13, 2007, now Pat. No. 7,637,660, which is a continuation of application No. 11/193,941, filed on Jul. 29, 2005, now Pat. No. 7,175,347, said application No. 13/304,006 is a continuation-in-part of application No. 13/250,754, filed on Sep. 30, 2011, now Pat. No. 8,971,482.

(60) Provisional application No. 60/670,164, filed on Apr. 11, 2005, provisional application No. 60/593,001, filed on Jul. 30, 2004, provisional application No. 61/388,487, filed on Sep. 30, 2010, provisional application No. 61/417,032, filed on Nov. 24, 2010.

(51) Int. Cl.
*A61B 6/04* (2006.01)
*G01N 23/04* (2006.01)
*A61B 5/055* (2006.01)
*A61B 6/10* (2006.01)

(56) References Cited

U.S. PATENT DOCUMENTS

| | | |
|---|---|---|
| 3,775,612 A | 11/1973 | Foster et al. |
| 3,904,878 A | 9/1975 | Burch et al. |
| 4,006,359 A | 2/1977 | Sullins et al. |
| 4,131,802 A | 12/1978 | Braden et al. |
| 4,928,283 A | 5/1990 | Gordon |
| 5,389,101 A | 2/1995 | Heilbrun et al. |
| 5,448,607 A | 9/1995 | McKenna |
| 5,736,821 A | 4/1998 | Suyama |
| 5,867,553 A | 2/1999 | Gordon et al. |
| 5,887,047 A | 3/1999 | Bailey et al. |
| 5,982,843 A | 11/1999 | Bailey et al. |
| 6,108,396 A | 8/2000 | Bechwati et al. |
| 6,144,180 A | 11/2000 | Chen et al. |
| 6,212,251 B1 | 4/2001 | Tomura et al. |
| 6,256,404 B1 | 7/2001 | Gordon et al. |
| 6,285,028 B1 | 9/2001 | Yamakawa |
| 6,374,937 B1 | 4/2002 | Galando et al. |
| 6,396,902 B2 | 5/2002 | Tybinkowski et al. |
| 6,459,923 B1 | 10/2002 | Plewes et al. |
| 6,705,758 B1 | 3/2004 | Luusua et al. |
| 6,813,374 B1 | 11/2004 | Karimi et al. |
| 6,857,778 B2 | 2/2005 | Mun et al. |
| 6,959,068 B1 | 10/2005 | Sommer |
| 7,175,347 B2 | 2/2007 | Tybinkowski et al. |
| 7,319,738 B2 | 1/2008 | Lasiuk et al. |
| 7,338,207 B2 | 3/2008 | Gregerson et al. |
| 7,396,160 B2 | 7/2008 | Tybinkowski et al. |
| 7,397,895 B2 | 7/2008 | Bailey et al. |
| 7,438,471 B2 | 10/2008 | Tybinkowski et al. |
| 7,568,836 B2 | 8/2009 | Bailey et al. |
| 7,637,660 B2 | 12/2009 | Tybinkowski et al. |
| 7,736,056 B2 | 6/2010 | Tybinkowski et al. |
| 7,963,696 B2 | 6/2011 | Bailey et al. |
| 8,118,488 B2 | 2/2012 | Gregerson |
| 8,251,584 B2 | 8/2012 | Tybinkowski et al. |
| 8,971,482 B2 * | 3/2015 | Bailey .................. A61B 6/03 378/20 |
| 2002/0035317 A1 | 3/2002 | Cheng et al. |
| 2003/0072613 A1 | 4/2003 | Colvard |
| 2003/0095635 A1 | 5/2003 | Moritake et al. |
| 2003/0147490 A1 | 8/2003 | Stabe et al. |
| 2003/0206609 A1 | 11/2003 | Kling et al. |
| 2005/0284672 A1 | 12/2005 | Egen et al. |
| 2006/0083354 A1 * | 4/2006 | Tybinkowski ......... A61B 6/032 378/198 |
| 2007/0183588 A1 | 8/2007 | Bailey et al. |
| 2007/0183589 A1 | 8/2007 | Tybinkowski et al. |
| 2007/0195938 A1 | 8/2007 | Bailey et al. |
| 2010/0172468 A1 | 7/2010 | Gregerson |
| 2011/0222667 A1 * | 9/2011 | Gregerson ............ A61B 6/035 378/198 |
| 2011/0228910 A1 | 9/2011 | Gregerson et al. |
| 2012/0256099 A1 | 10/2012 | Gregerson et al. |
| 2012/0330087 A1 | 12/2012 | Gregerson |

FOREIGN PATENT DOCUMENTS

| | | |
|---|---|---|
| JP | 2002085394 | 3/2002 |
| JP | 2003-190149 | 7/2003 |
| WO | WO 98/00681 | 7/1999 |

* cited by examiner

CereTom® CT Machine

BodyTom™ CT Machine (Rear)

BodyTom™ CT Machine (Rear)

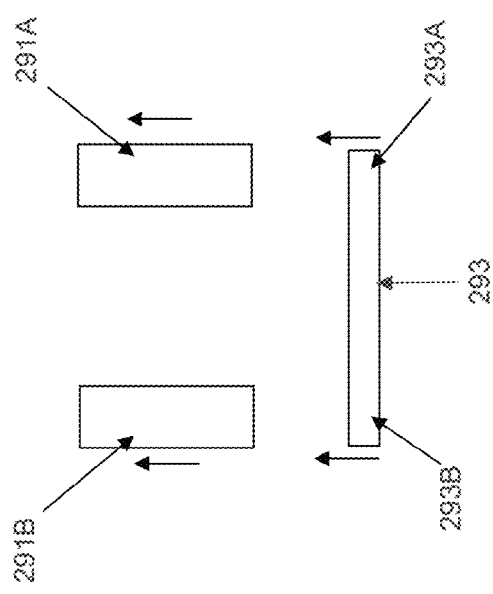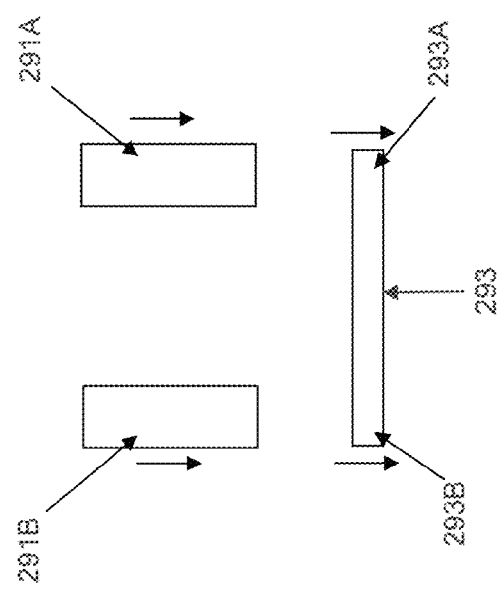
FIG. 22A
FIG. 22B

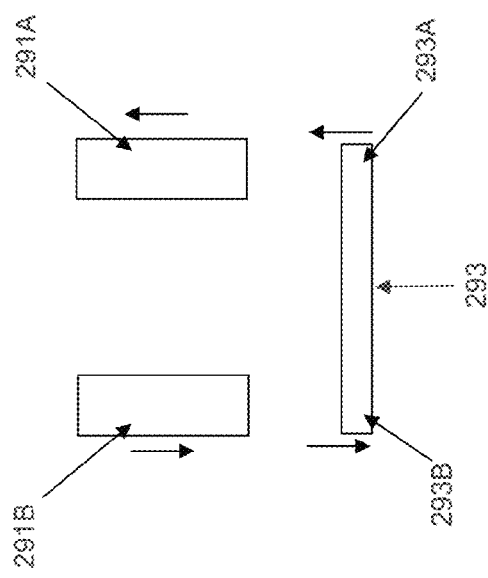
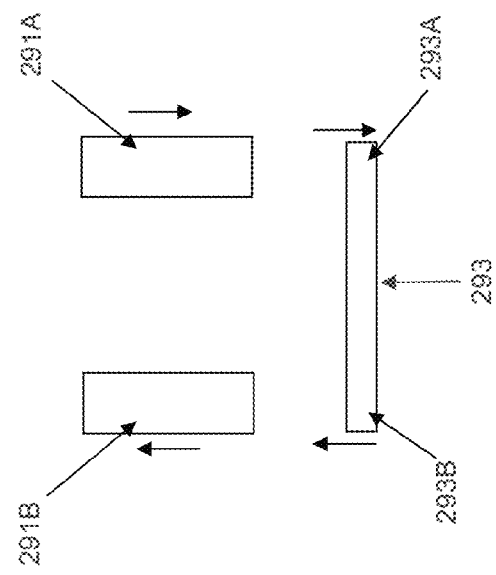
FIG. 22C
FIG. 22D

ANATOMICAL IMAGING SYSTEM WITH CENTIPEDE SCANNING DRIVE, BOTTOM NOTCH TO ACCOMMODATE BASE OF PATIENT SUPPORT, AND MOTORIZED DRIVE FOR TRANSPORTING THE SYSTEM BETWEEN SCANNING LOCATIONS

REFERENCE TO PRIOR PATENT APPLICATIONS

This patent application is a continuation of pending prior U.S. patent application Ser. No. 13/304,006, filed Nov. 23, 2011 by Eric Bailey et al. for ANATOMICAL IMAGING SYSTEM WITH CENTIPEDE SCANNING DRIVE, BOTTOM NOTCH TO ACCOMMODATE BASE OF PATIENT SUPPORT, AND MOTORIZED DRIVE FOR TRANSPORTING THE SYSTEM BETWEEN SCANNING LOCATIONS, which in turn:

(i) is a continuation-in-part of prior U.S. patent application Ser. No. 12/655,360, filed Dec. 29, 2009 by Andrew P. Tybinkowski et al. for ANATOMICAL IMAGING SYSTEM WITH CENTIPEDE BELT DRIVE, which is a continuation of prior U.S. patent application Ser. No. 11/706,133, filed Feb. 13, 2007 by Andrew P. Tybinkowski et al. for ANATOMICAL IMAGING SYSTEM WITH CENTIPEDE BELT DRIVE, which is a continuation of prior U.S. patent application Ser. No. 11/193,941, filed Jul. 29, 2005 by Andrew P. Tybinkowski et al. for ANATOMICAL IMAGING SYSTEM WITH CENTIPEDE BELT DRIVE, which claims benefit of (a) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE; and (b) prior U.S. Provisional Patent Application Ser. No. 60/593,001, filed Jul. 30, 2004 by Bernard Gordon et al. for ANATOMICAL SCANNING SYSTEM;

(ii) is a continuation-in-part of pending prior U.S. patent application Ser. No. 13/250,754, filed Sep. 30, 2011 by Eric Bailey et al. for ANATOMICAL IMAGING SYSTEM WITH CENTIPEDE BELT DRIVE AND BOTTOM NOTCH TO ACCOMMODATE BASE OF PATIENT SUPPORT, which claims benefit of prior U.S. Provisional Patent Application Ser. No. 61/388,487, filed Sep. 30, 2010 by Eric Bailey et al. for ANATOMICAL IMAGING SYSTEM WITH CENTIPEDE BELT DRIVE AND BOTTOM NOTCH TO ACCOMMODATE BASE OF PATIENT SUPPORT; and (iii) claims benefit of prior U.S. Provisional Patent Application Ser. No. 61/417,032, filed Nov. 24, 2010 by Eric Bailey et al. for ANATOMICAL IMAGING SYSTEM WITH CENTIPEDE BELT DRIVE AND BOTTOM NOTCH TO ACCOMMODATE BASE OF PATIENT SUPPORT.

The above-identified patent applications are hereby incorporated herein by reference.

FIELD OF THE INVENTION

This invention relates to imaging systems in general, and more particularly to anatomical imaging systems.

BACKGROUND OF THE INVENTION

CereTom® CT Machine with Centipede Belt Drive

Looking first at FIGS. 1-4, there is shown a CereTom® CT machine 5 made by Neurologica Corp. of Danvers, Mass. CereTom® CT machine 5 is a relatively small, mobile CT machine which is intended to be brought to the patient so that the patient can be scanned at the patient's current location, rather than requiring that the patient be transported to the location of a CT machine, so as to facilitate more rapid and/or more convenient scanning of the patient.

CereTom® CT machine 5 generally comprises a torus 10 which is supported by a base 15. A center opening 20 is formed in torus 10. Center opening 20 receives the patient anatomy which is to be scanned by CereTom® CT machine 5. Inasmuch as CereTom® CT machine 5 is designed to be as small and mobile as possible, and inasmuch as CereTom® CT machine 5 is intended to be used extensively for stroke diagnosis applications, center opening 20 is configured to be just slightly larger than the head of a patient.

Looking next at FIG. 3, torus 10 of CereTom® CT machine 5 generally comprises an X-ray tube assembly 25, an X-ray detector assembly 30, and a rotating drum assembly 35. X-ray tube assembly 25 and X-ray detector assembly 30 are mounted to rotating drum assembly 35 in diametrically-opposed relation, such that the X-ray beam 40 (generated by X-ray tube assembly 25 and detected by X-ray detector assembly 30) is passed through the patient anatomy which is disposed in center opening 20. Significantly, inasmuch as X-ray tube assembly 25 and X-ray detector assembly 30 are mounted on rotating drum assembly 35 so that they rotate concentrically about center opening 20, X-ray beam 40 will be passed through the patient's anatomy along a full range of radial positions, so as to enable CereTom® CT machine 5 to create a visual rendition of the scanned anatomy using computerized tomography algorithms of the sort well known in the art.

Still looking at FIG. 3, the various electronic hardware and software for controlling the operation of X-ray tube assembly 25, X-ray detector assembly 30, and rotating drum assembly 35, as well as for processing the acquired scan data so as to generate the desired visual rendition of the scanned anatomy, are located in torus 10 and/or base 15.

Looking next at FIGS. 3 and 4, base 15 of CereTom® CT machine 5 comprises a transport assembly 50 for moving the CereTom® CT machine 5 relative to the patient. More particularly, transport assembly 50 comprises a gross movement mechanism 55 for moving CereTom® CT machine 5 relatively quickly across room distances, and a fine movement mechanism 60 for moving CereTom® CT machine 5 precisely, relative to the patient, during scanning. Gross movement mechanism 55 preferably comprises a plurality of casters 62, and fine movement mechanism 60 preferably comprises a plurality of centipede belt drives 63. Hydraulic apparatus 65 permits either gross movement mechanism 55, or fine movement mechanism 60, to be engaged with the floor, whereby to facilitate appropriate movement of CereTom® CT machine 5. Thus, with CereTom® CT machine 5, the CT machine may be pre-positioned in an "out of the way" location in an emergency room and then, when a patient requires scanning, the patient may be scanned right at their bedside, by quickly moving the CT machine to the patient's bedside on gross movement mechanism 55 (e.g., casters 62), and thereafter moving the machine during scanning on fine movement mechanism 60 (e.g., centipede belt drives 63).

Looking again at FIG. 3, base 15 also includes other system components in addition to those discussed above, e.g., batteries 70 for powering various electrical components of CereTom® CT machine 5, etc.

As noted above, the various components of CereTom® CT machine 5 are engineered so as to provide a relatively small and mobile CT machine. As a result, CereTom® CT machine 5 is particularly well suited for use in stroke diagnosis applications. More particularly, since CereTom® CT machine 5 is constructed so as to be a small, mobile unit, it can be pre-positioned in the emergency room of a hospital and then quickly moved to the bedside of a patient when scanning is required, rather than requiring the patient to be transported to a radiology department for scanning. Furthermore, the patient can be scanned while remaining on their hospital bed or gurney, since CereTom® CT machine 5 moves relative to the patient during scanning. This is extremely beneficial, since it eliminates transport delays and hence significantly reduces the time needed to scan the patient, which can be extremely important in timely diagnosing a potential stroke victim.

Further details regarding the construction and use of CereTom® CT machine 5 are disclosed in U.S. Pat. Nos. 7,175,347, 7,637,660, 7,568,836, 7,963,696, 7,438,471, 7,397,895, 7,396,160 and 7,736,056, which patents are hereby incorporated herein by reference.

Operating Room Applications

In practice, CereTom® CT machine 5 has proven to be highly effective in the timely diagnosis of potential stroke victims. In addition, CereTom® CT machine 5 has also proven to be highly effective in other head scanning applications, in the scanning of limbs (e.g., arms and/or hands, legs and/or feet), and in scanning infants and small toddlers (e.g., those capable of fitting within center opening 20). Furthermore, CereTom® CT machine 5 has also proven highly effective in veterinarian applications (e.g., to scan the leg and/or hoof of a horse).

Significantly, in view of the relatively small size and high mobility of CereTom® CT machine 5, CT scanning has been conducted in a wide range of different locations, e.g., in emergency rooms for stroke diagnosis, in operating rooms for neurosurgical applications, in veterinary clinics for animal treatment, etc.

In view of the substantial success of CereTom® CT machine 5, it has now been desired to increase the size of CereTom® CT machine 5 so that it can be used for full body scanning, e.g., such as during a spinal procedure in an operating room. To this end, it is necessary for CereTom® CT machine 5 to be scaled up in size so that the diameter of center opening 20 is large enough to receive both the torso of the patient and the surgical platform needed to support the patient during the surgical procedure. However, in this respect, it must also be appreciated that additional changes must be made to CereTom® CT machine 5 in order to permit the aforementioned full body scanning in an operating room setting.

More particularly, in FIGS. 5-7 there is shown a typical patient support 100 for supporting a patient during a surgical procedure. Patient support 100 generally comprises a horizontally-extending surgical platform 105 for receiving and supporting the patient. Horizontally-extending surgical platform 105 is supported above the ground by a horizontally-extending base 110 and a vertically-extending riser 115. It will be appreciated that horizontally-extending surgical platform 105 essentially comprises a cantilever beam arrangement. It will also be appreciated that, in view of the substantial length of horizontally-extending surgical platform 105, and also the substantial weight associated with horizontally-extending surgical platform 105 (particularly when a patient is lying on surgical platform 105), horizontally-extending base 110 must generally have a substantial length and a substantial mass in order to prevent patient support 100 from tipping over. In other words, in practice, the "head end" 120 of horizontally-extending base 110 must extend a substantial distance away from the "foot end" 125 of horizontally-extending base 110, and horizontally-extending base 110 must have a substantial mass in order to prevent patient support 100 from tipping over. This substantial mass for horizontally-extending base 110 is typically provided by giving the base a relatively substantial width 127 and a relatively substantial height 128.

Unfortunately, and as seen in FIGS. 1-4, base 15 of CereTom® CT machine 5 has a bottom skirt 75 which is disposed very close to the floor when CereTom® CT machine 5 is in its "scanning mode", i.e., when CereTom® CT machine 5 is supported by, and moves on, its fine movement mechanism 60 (e.g., centipede belt drives 63). As a result, simply scaling an existing CereTom® CT machine 5 upward in size to the point where central opening 20 can receive the torso of a patient (and surgical platform 105) will not result in a scanning machine which is capable of scanning the patient on patient support 100, since skirt 75 of base 15 of CereTom® CT machine 5 would engage the "head end" 120 of horizontally-extending base 110 of patient support 100 before CereTom® CT machine 5 can encompass the patient's torso (and surgical platform 105) in its central opening 20. In this respect it should be appreciated that the bottom of skirt 75 of CereTom® CT machine 5 is substantially even about the perimeter of the machine (i.e., the gap between the bottom of skirt 75 and the floor is substantially uniform about the entire perimeter of the machine). Furthermore, it should also be appreciated that with CereTom® CT machine 5, the bottom of skirt 75 is disposed relatively close to the surface of the floor, in order to prevent the feet of personnel from getting under the machine and in order to protect the components of the machine from collisions with objects, dust, etc. In fact, when CereTom® CT machine 5 is supported on its centipede belt drives 63, the bottom of skirt 75 sits approximately 2.2 inches above the surface of the floor.

Thus there is a need for a new and improved form of CereTom® CT machine 5 which can be used to scan the torso of a patient while the patient is supported on patient support 100.

In addition to the foregoing, as noted above, in order to enable a CereTom® CT machine 5 to be used for full body scanning, it is necessary to significantly increase the size of the machine. This can make it difficult to manually move the enlarged machine on its gross movement mechanism 55 (e.g., casters 62).

Thus there is a need to provide a new and improved form of CereTom® CT machine 5 which includes a motorized drive for transporting the system between scanning locations.

SUMMARY OF THE INVENTION

These and other objects of the present invention are addressed by the provision and use of a new and improved form of CereTom® CT machine 5, which can be used to scan the torso of a patient while the patient is supported on patient support 100, and which can include a motorized drive for transporting the system between scanning locations.

In one preferred form of the invention, there is provided an imaging system comprising:
a scanner for scanning an object and creating an image of the same; and a transport mechanism mounted to the scanner for moving the scanner, wherein the transport mechanism comprises:
  a gross movement mechanism for transporting the scanner between scanning locations; and
  a fine movement mechanism for moving the scanner precisely, relative to the object being scanned, during scanning of the object;
wherein the gross movement mechanism comprises at least one motorized wheel.

In another preferred form of the invention, there is provided a method for imaging an object, the method comprising:
  providing an imaging system comprising:
    a scanner for scanning an object and creating an image of the same; and
    a transport mechanism mounted to the scanner for moving the scanner, wherein the transport mechanism comprises:
      a gross movement mechanism for transporting the scanner between scanning locations; and
      a fine movement mechanism for moving the scanner precisely, relative to the object being scanned, during scanning of the object;
    wherein the gross movement mechanism comprises at least one motorized wheel;
  moving the scanner on the gross movement mechanism; and
  scanning the object while moving the scanner precisely, relative to the object, with the fine movement mechanism.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 16-26 are schematic views showing another novel BodyTom™ CT machine also formed in accordance with the present invention.

DETAILED DESCRIPTION OF THE PREFERRED EMBODIMENTS

In accordance with the present invention, there is now provided a new and improved form of CereTom® CT machine 5, hereinafter sometimes referred to as the BodyTom™ CT machine, which can be used to scan the torso of a patient while the patient is supported on patient support 100, and which can include a motorized drive for transporting the system between scanning locations.

Figure 5:
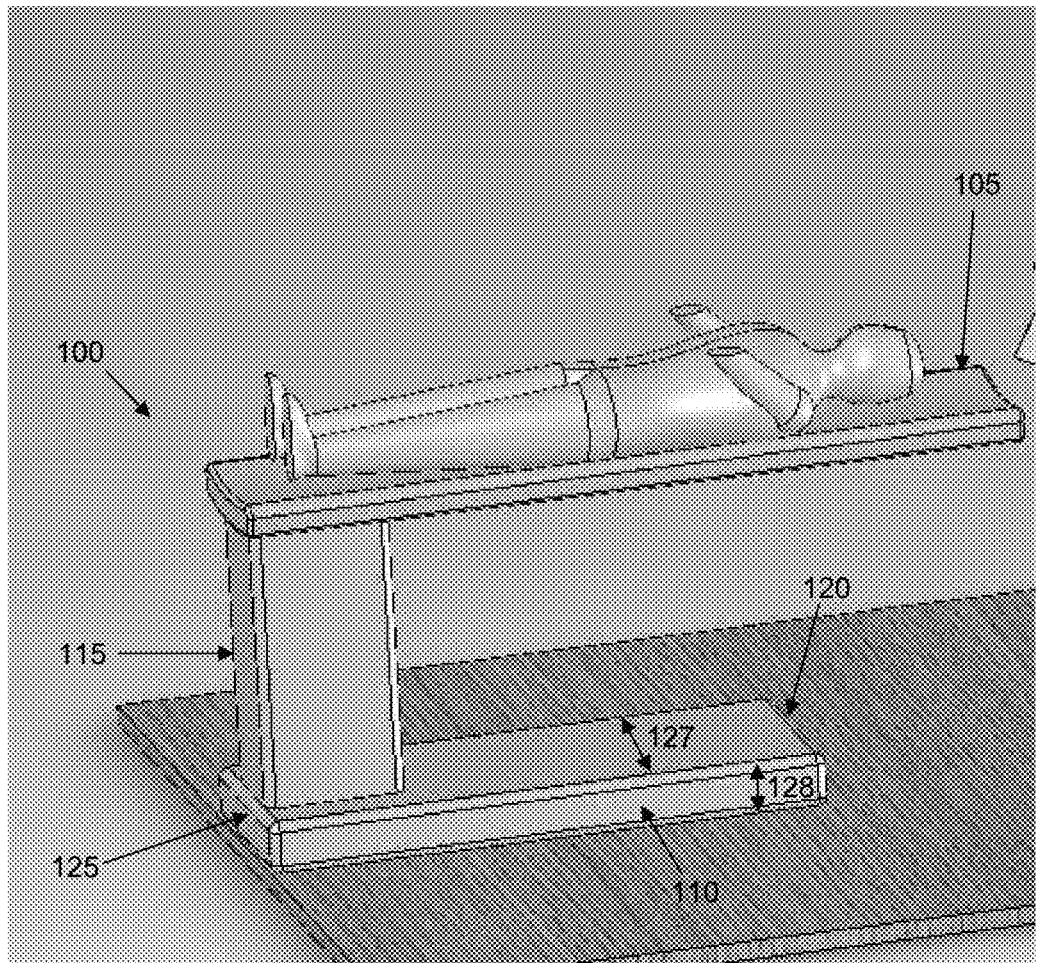
FIGS. 5-7 are schematic views showing a typical patient support for supporting a patient during a surgical procedure.
Figure 6:
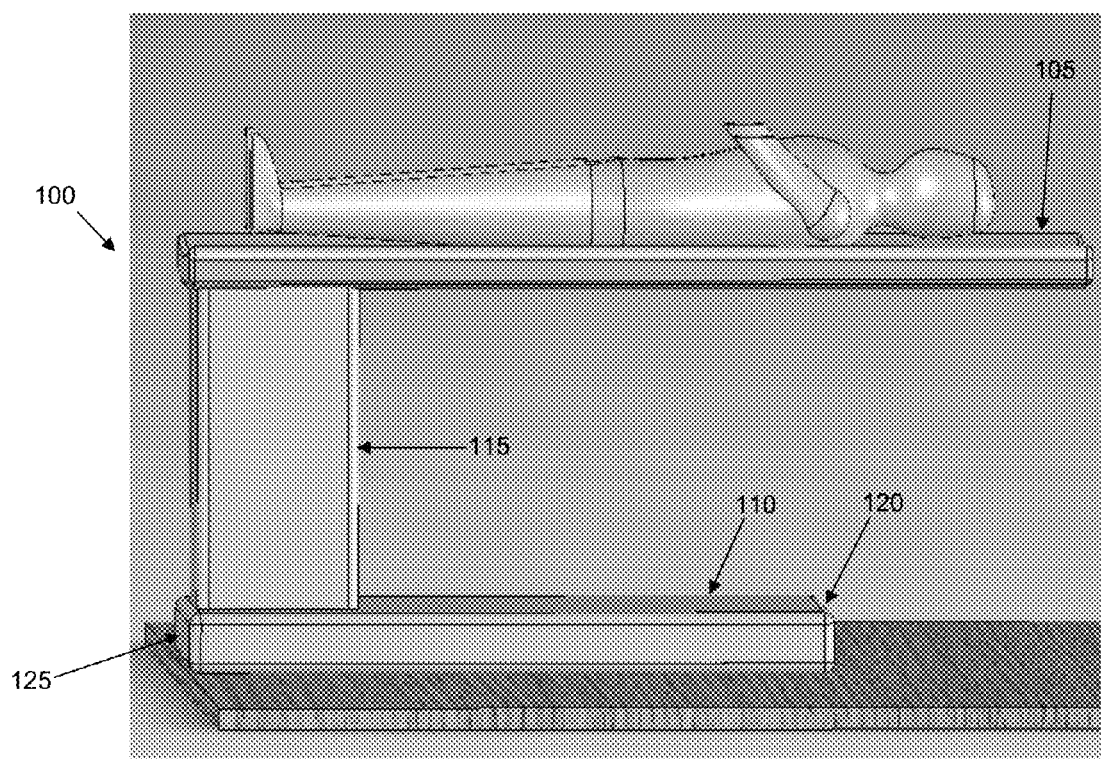
Figure 7:
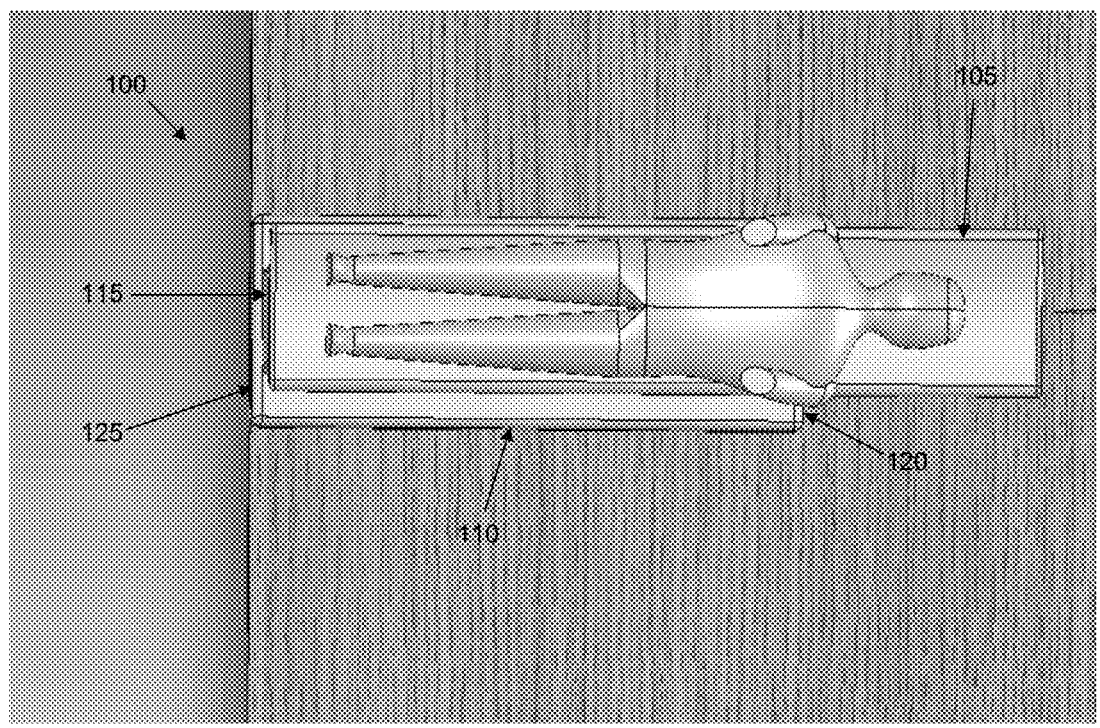
Figure 8:
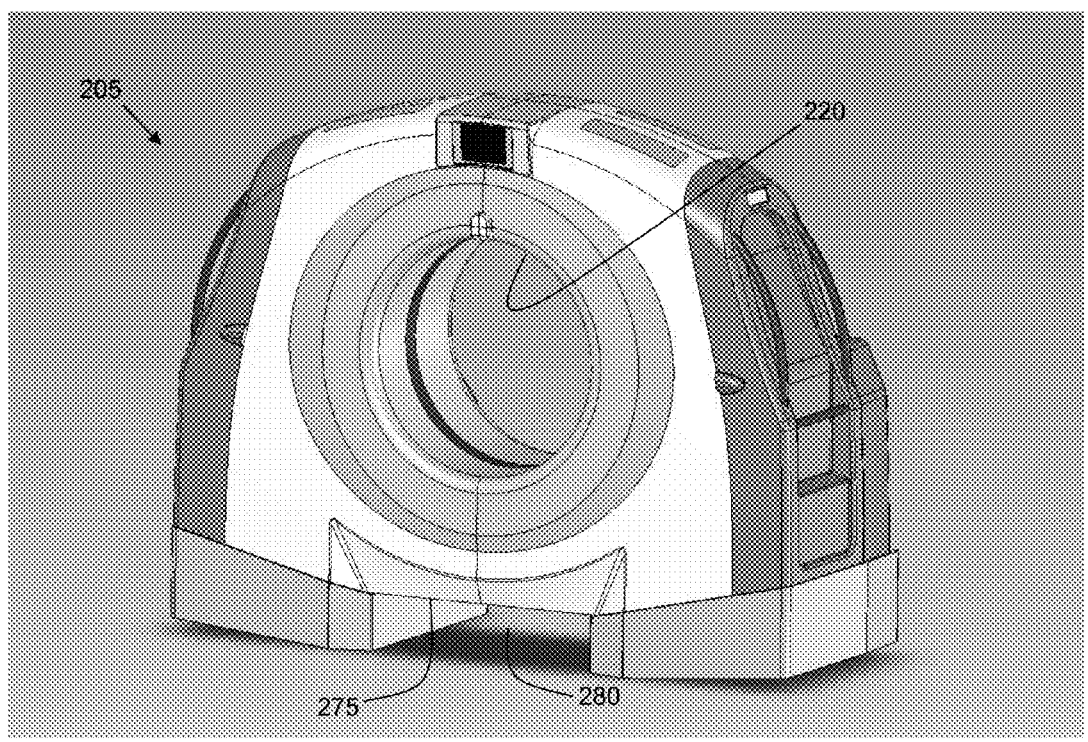
FIGS. 8-15 are schematic views showing a novel BodyTom™ CT machine formed in accordance with the present invention.
Figure 9:
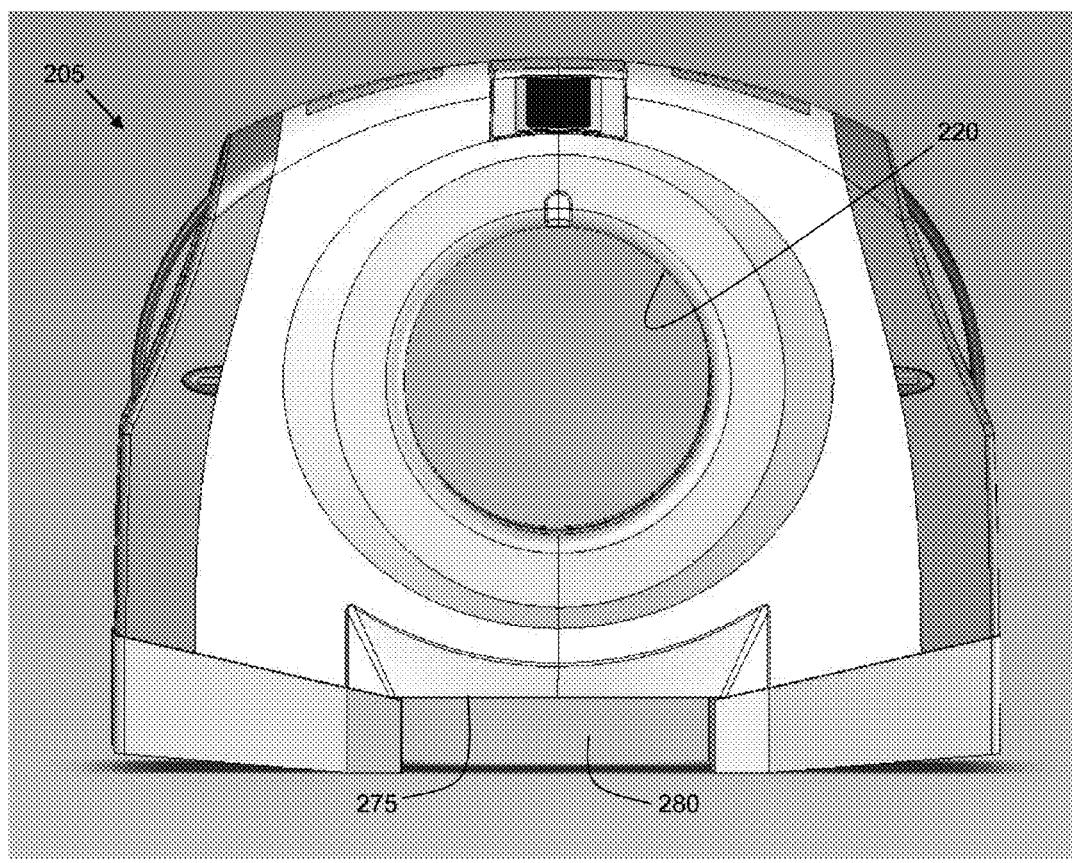
Figure 10:
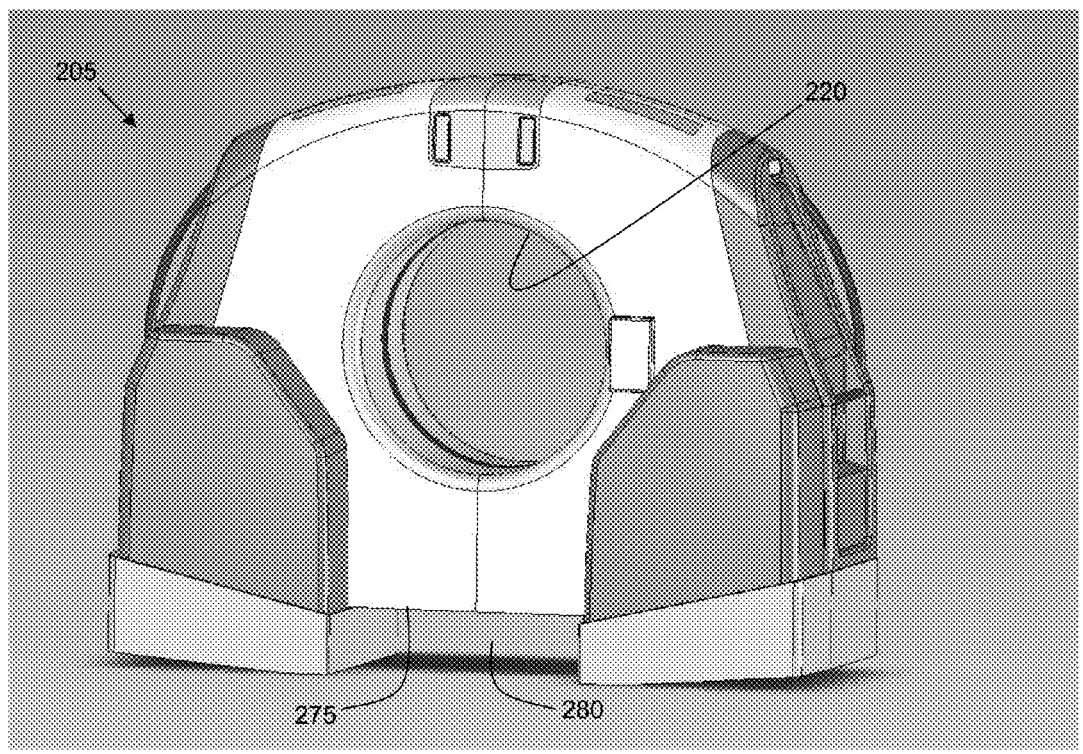
Figure 11:
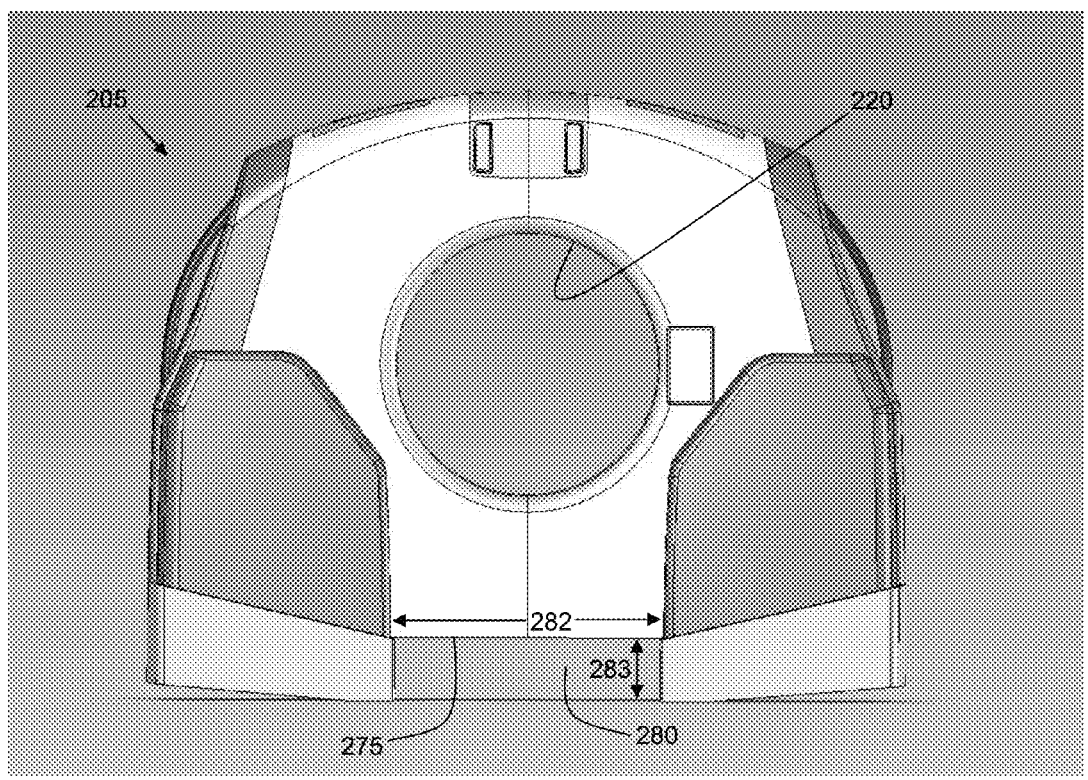
Figure 12:
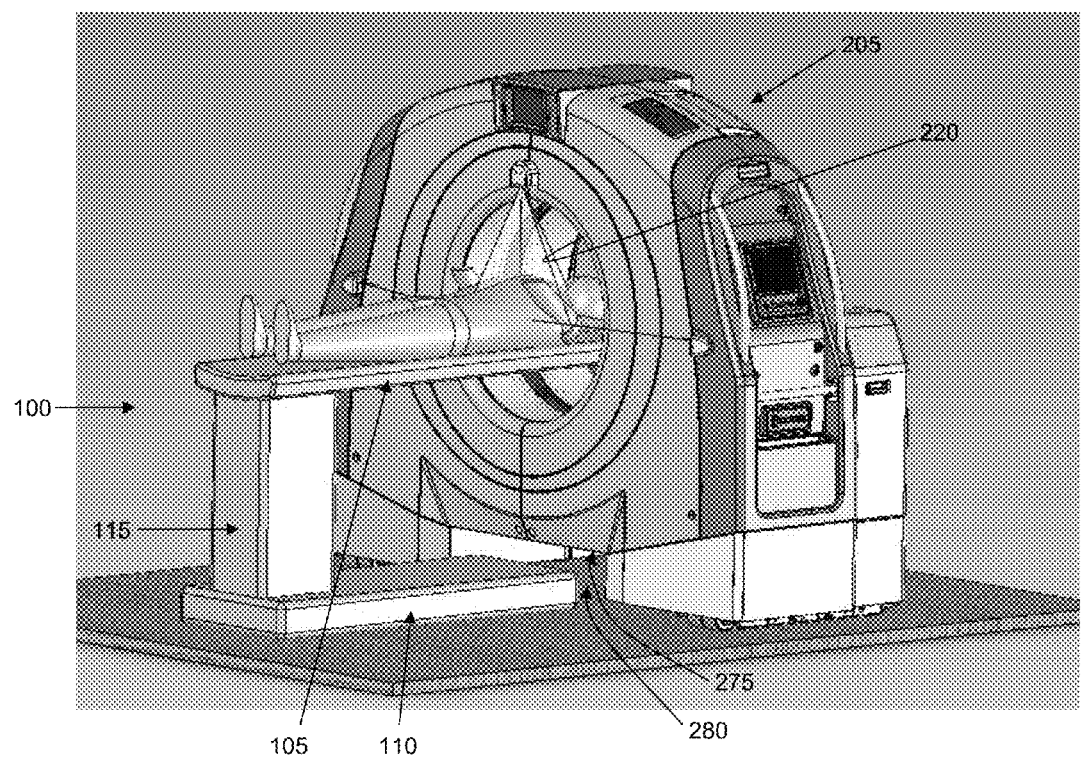
Figure 13:
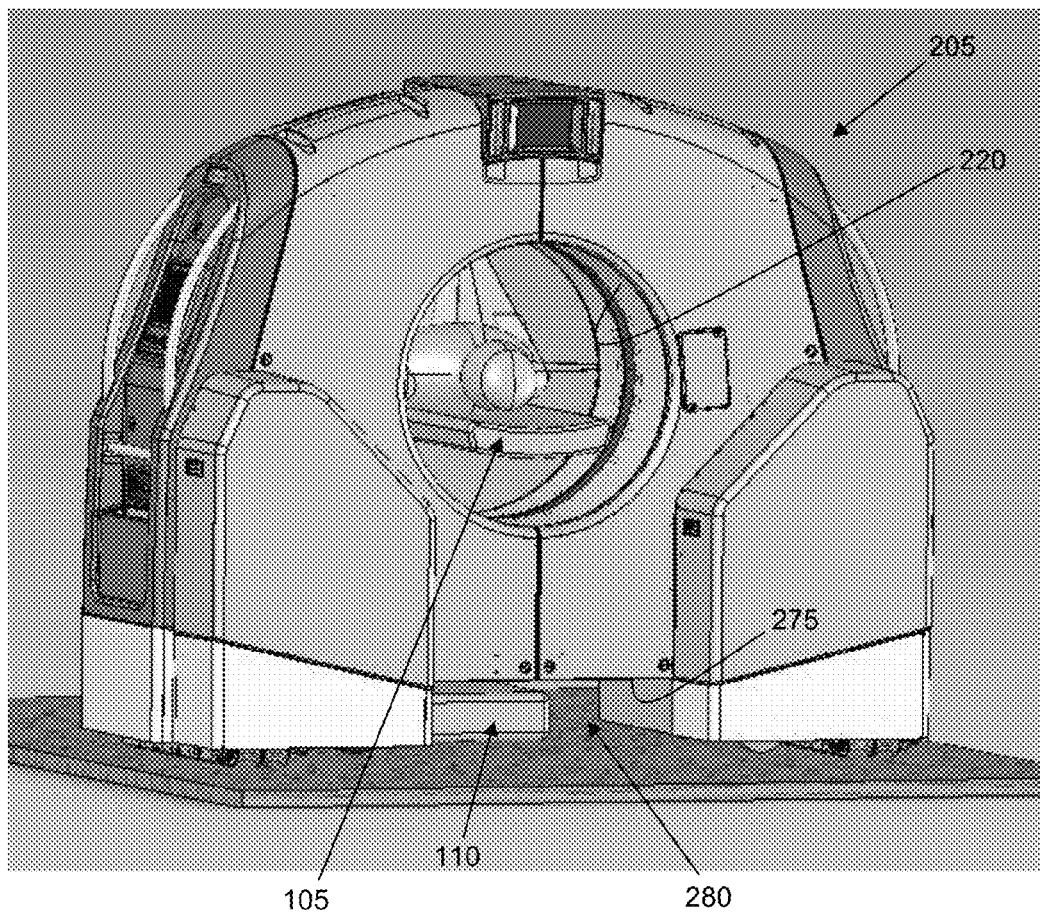
Figure 14:
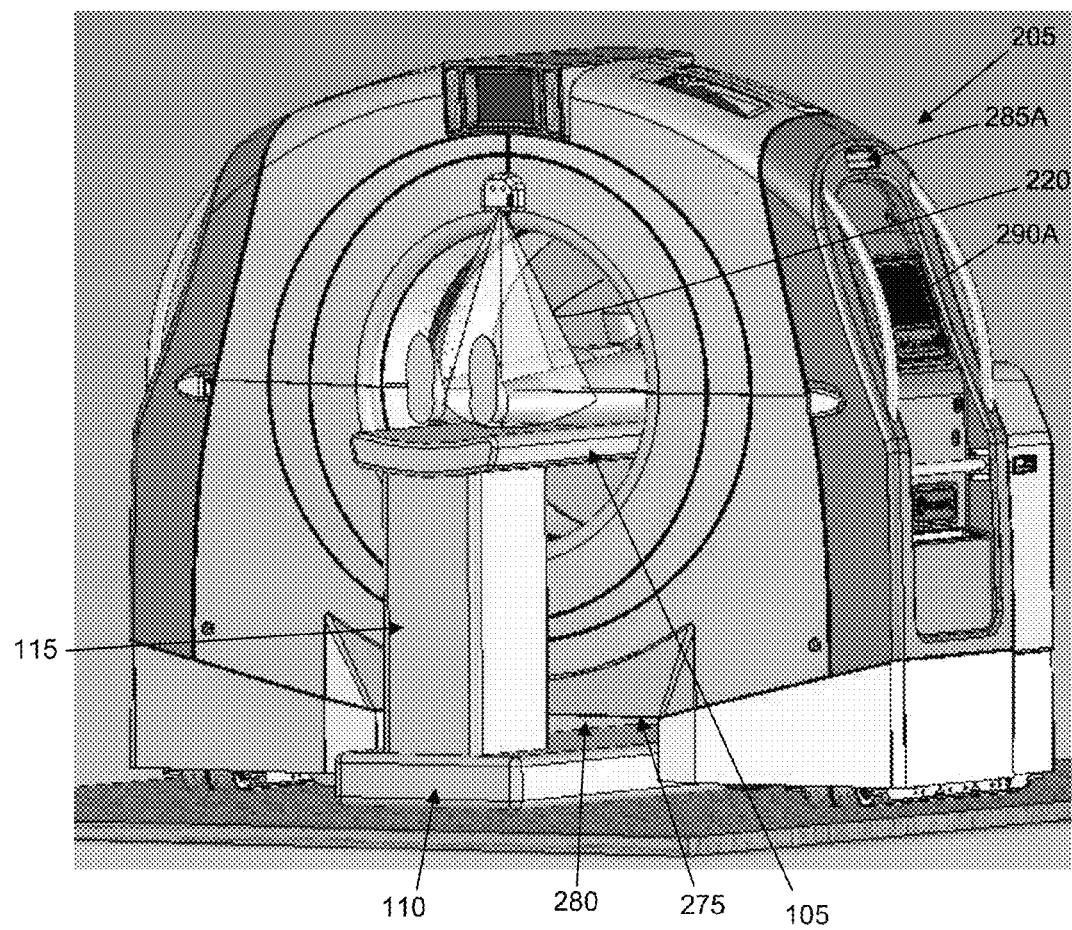
Figure 15:
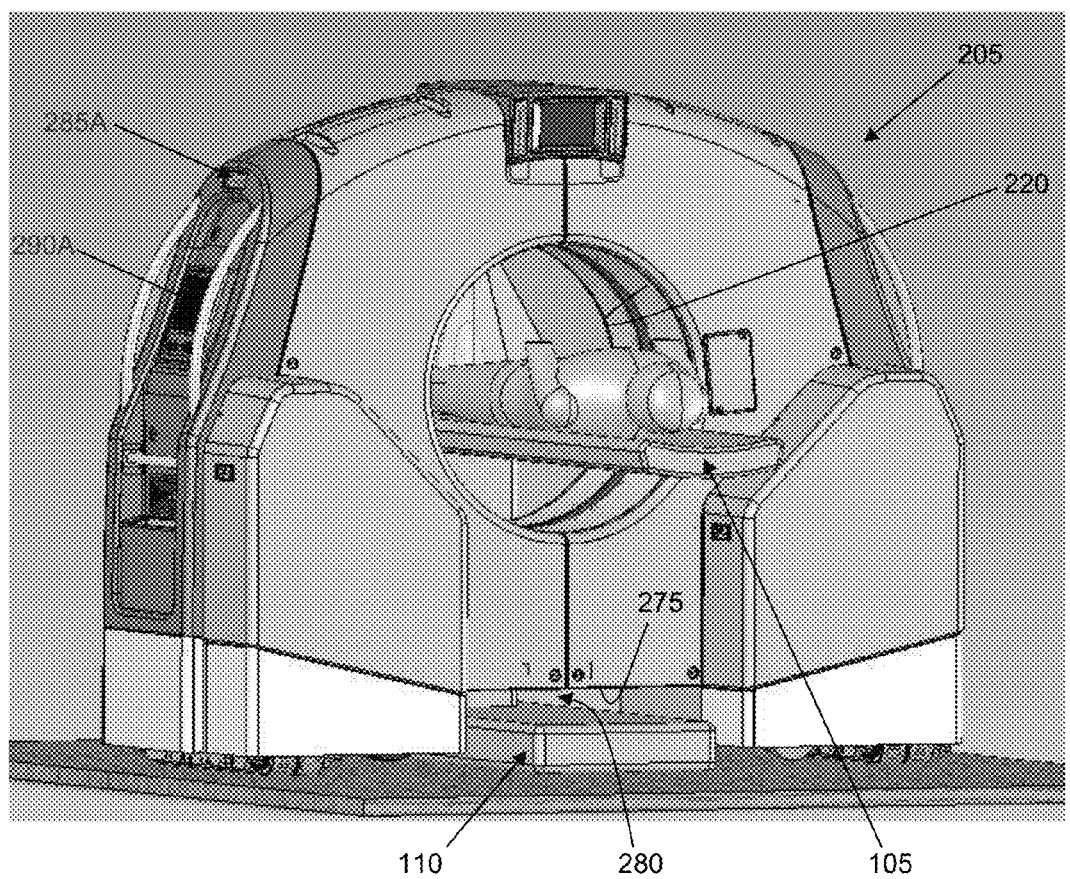
Figure 16:
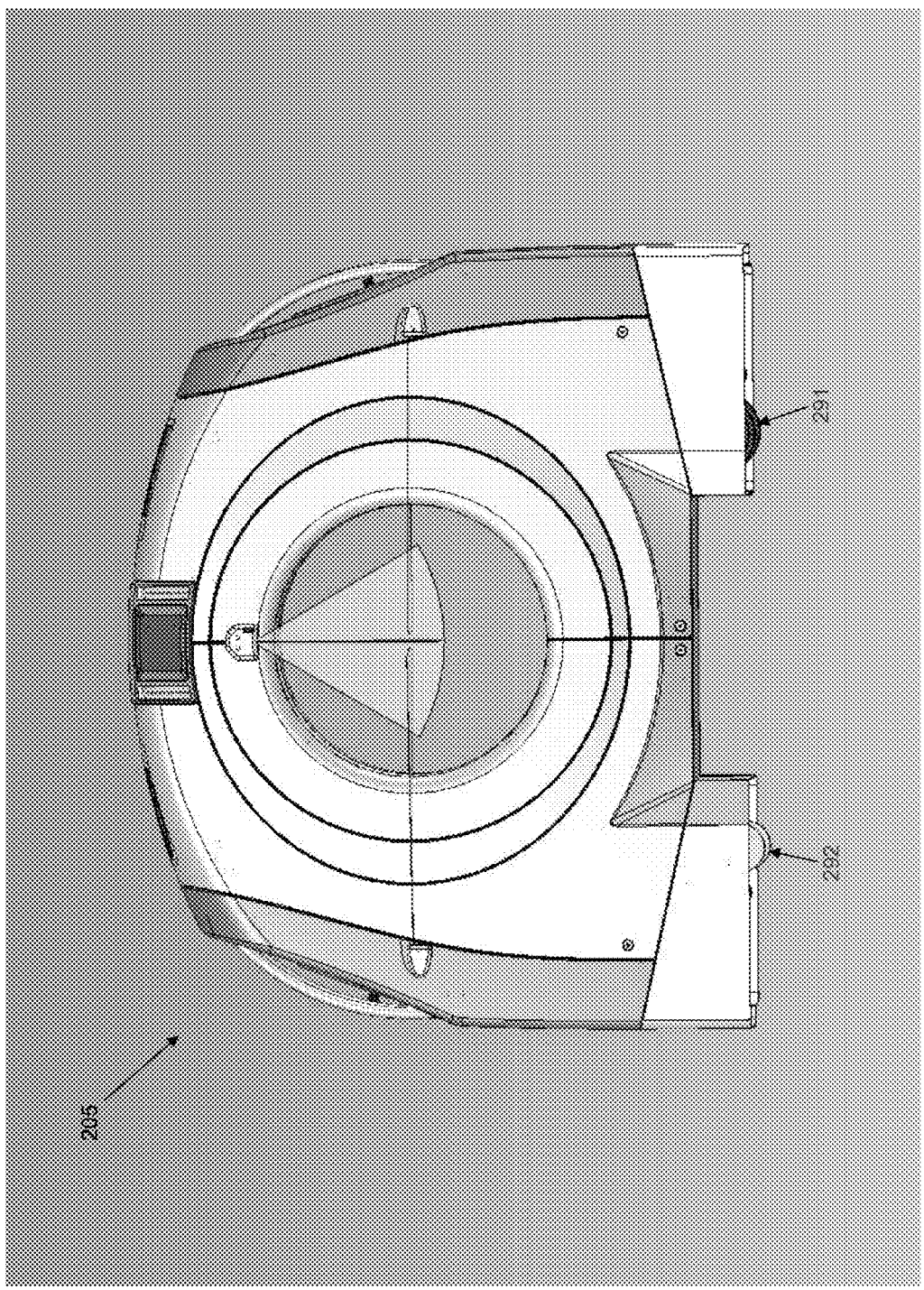
Figure 17:
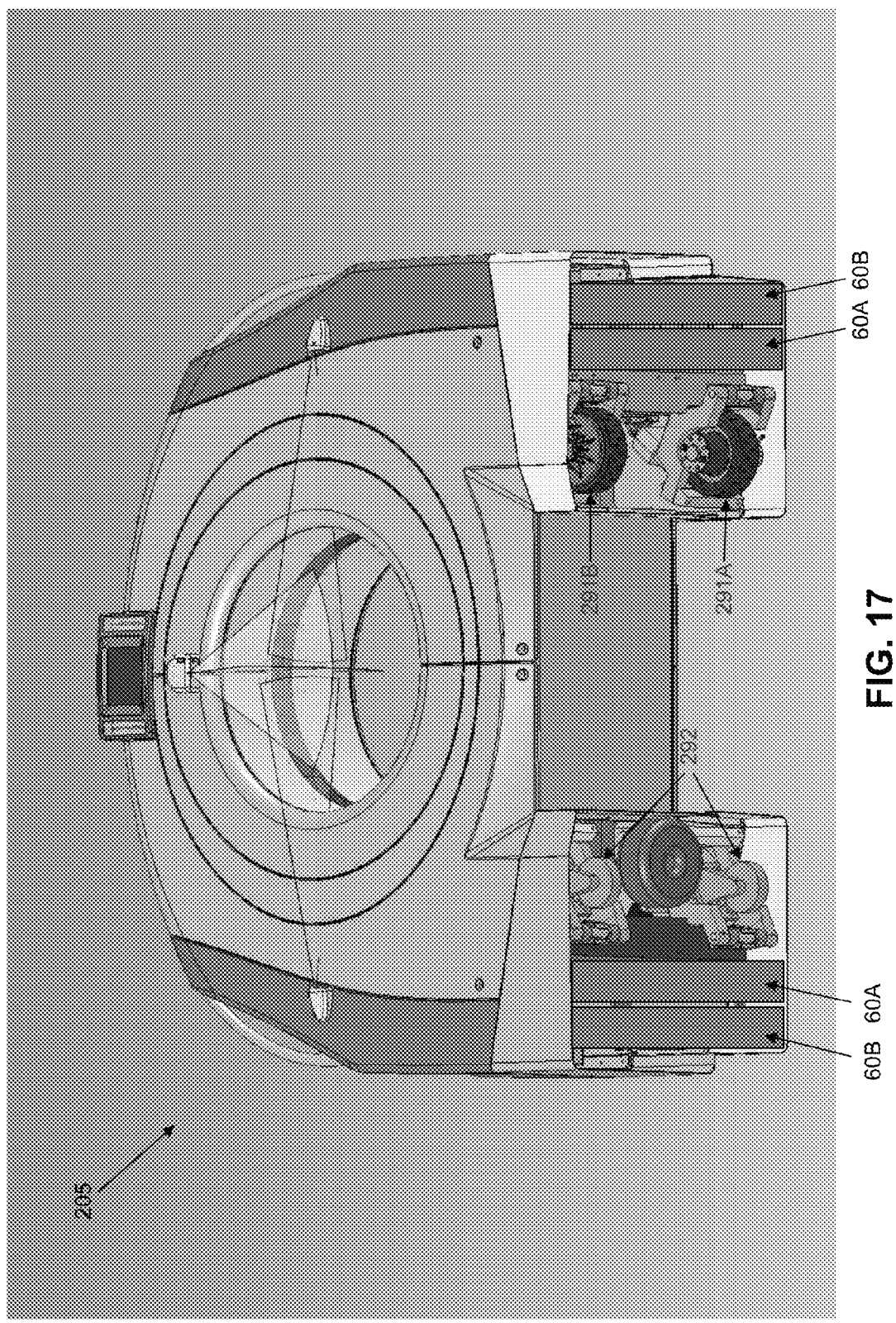
Figure 18:
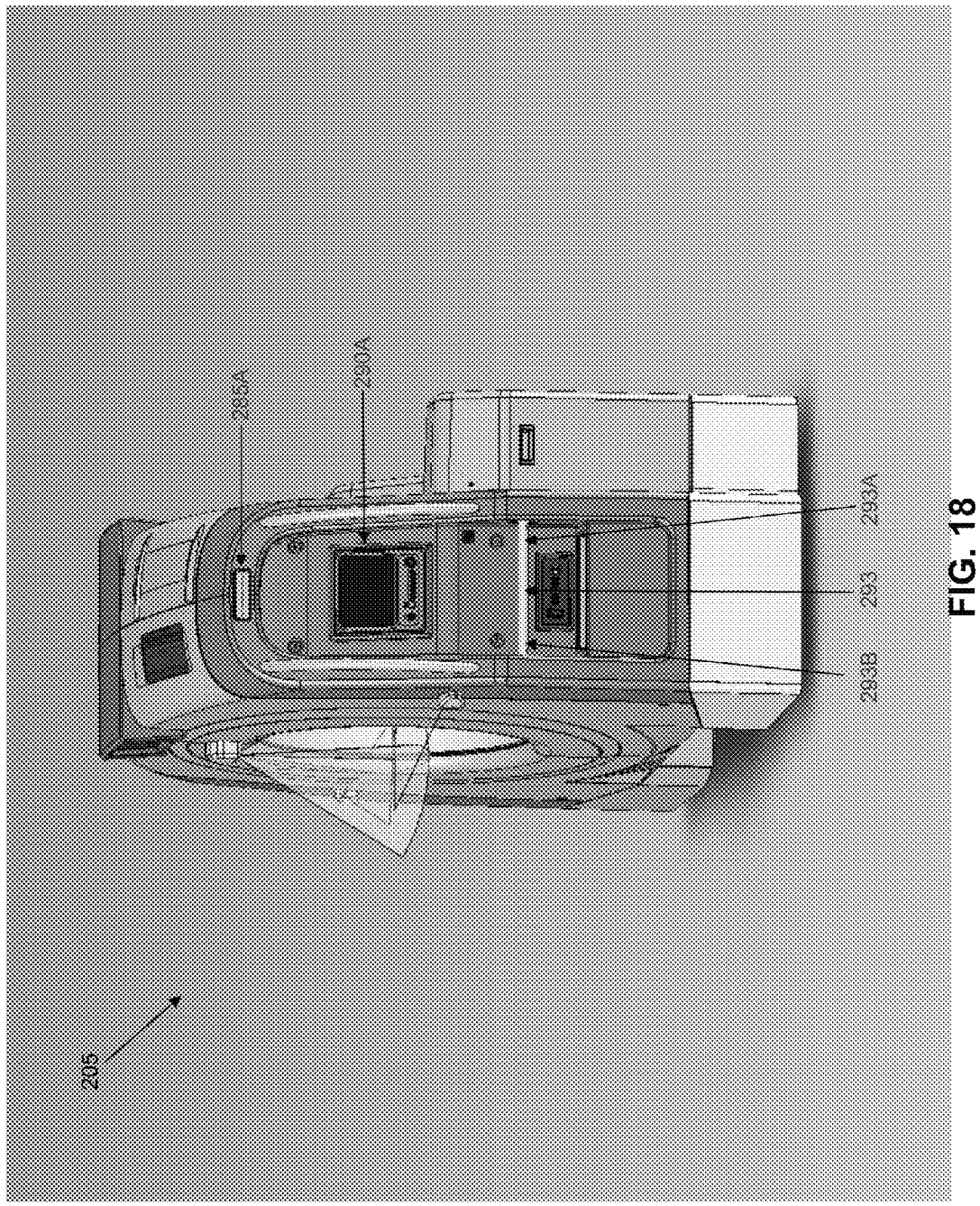
Figure 19:
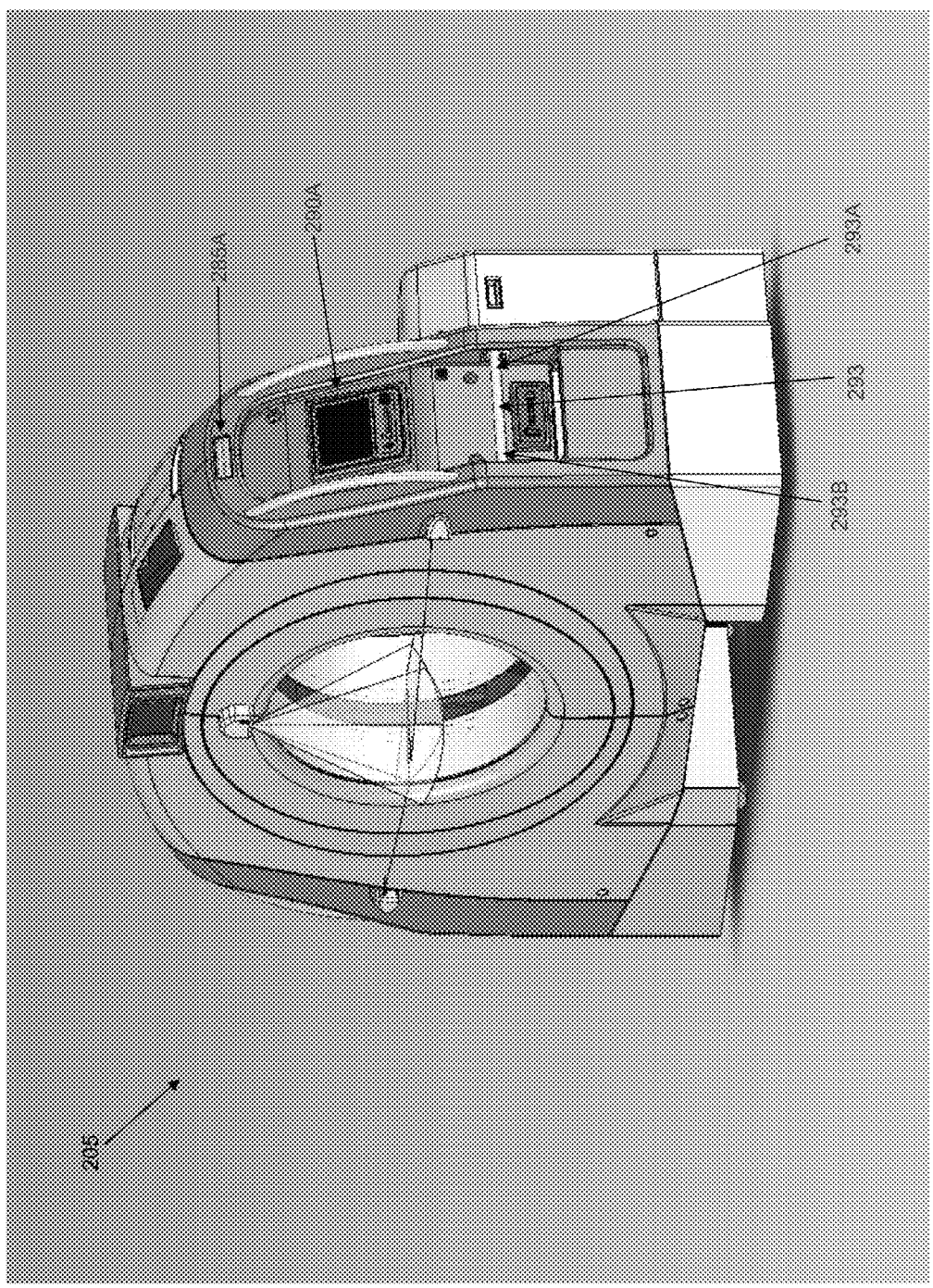
Figure 20:
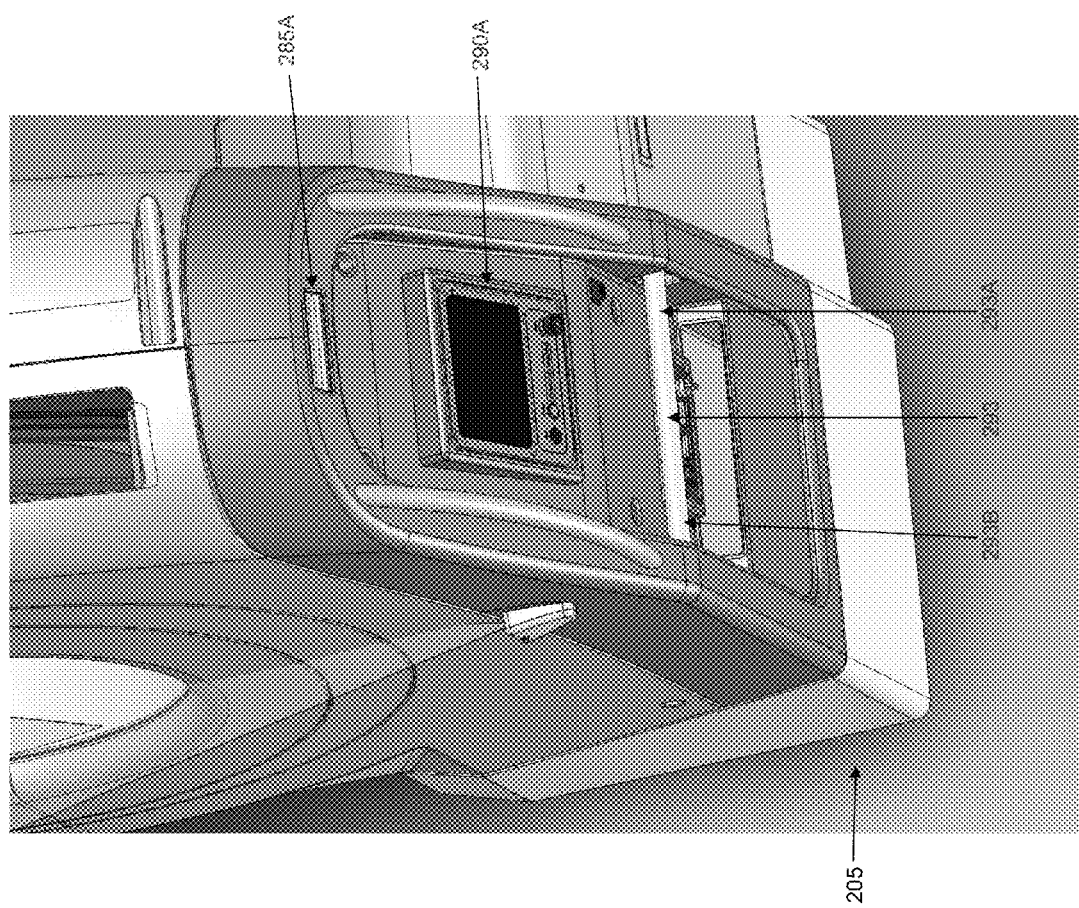
Figure 21:
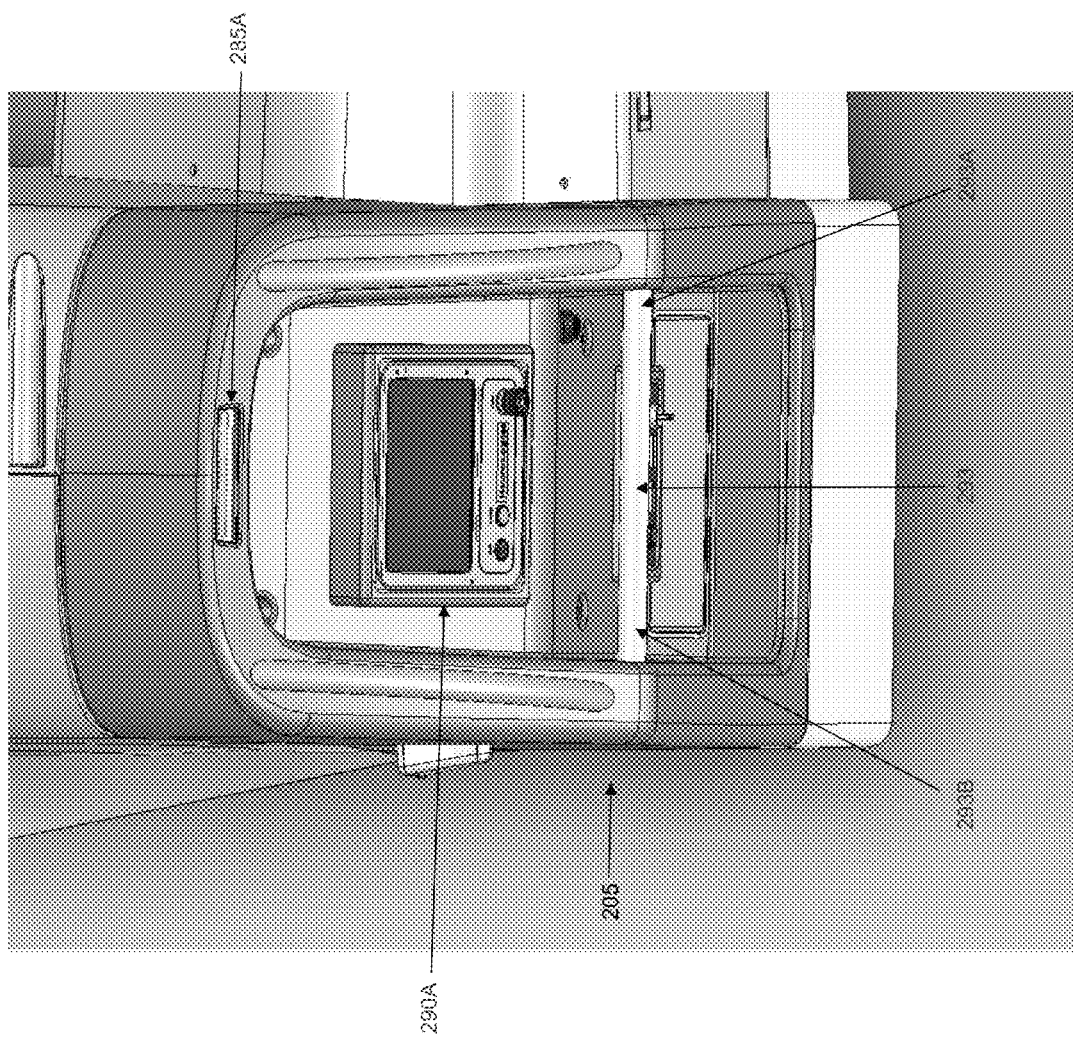
Figure 23:
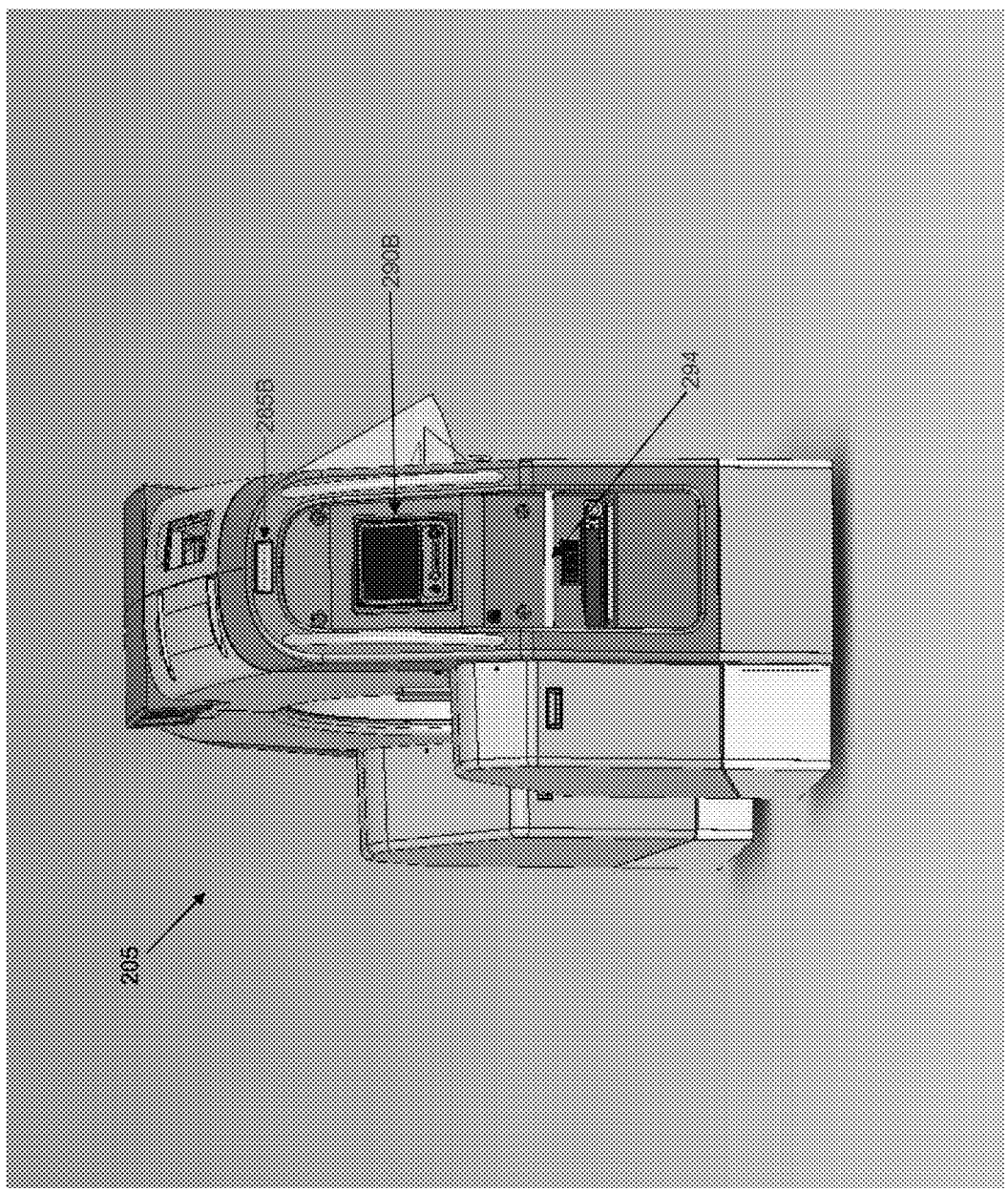
Figure 24:
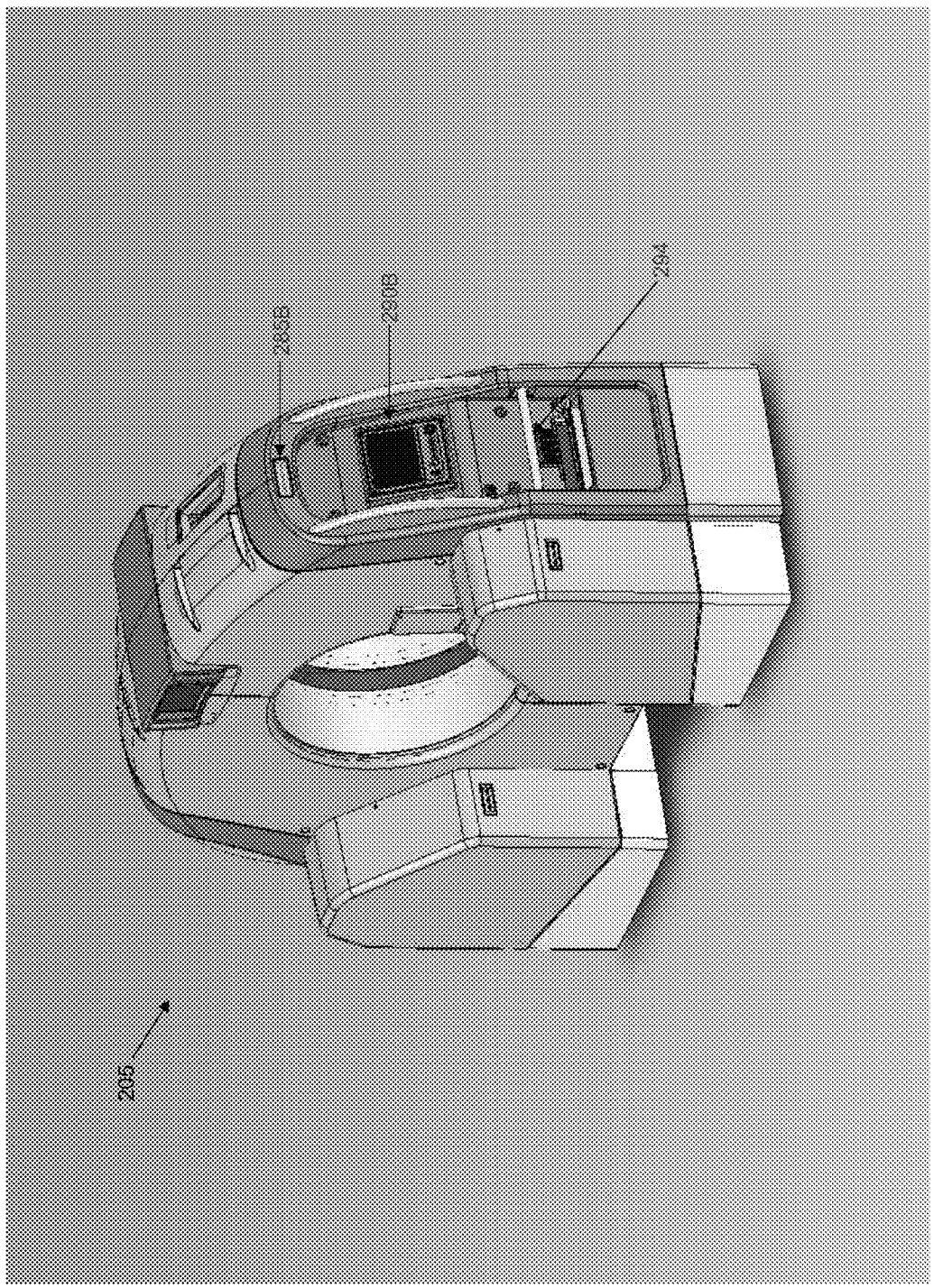
Figure 25:
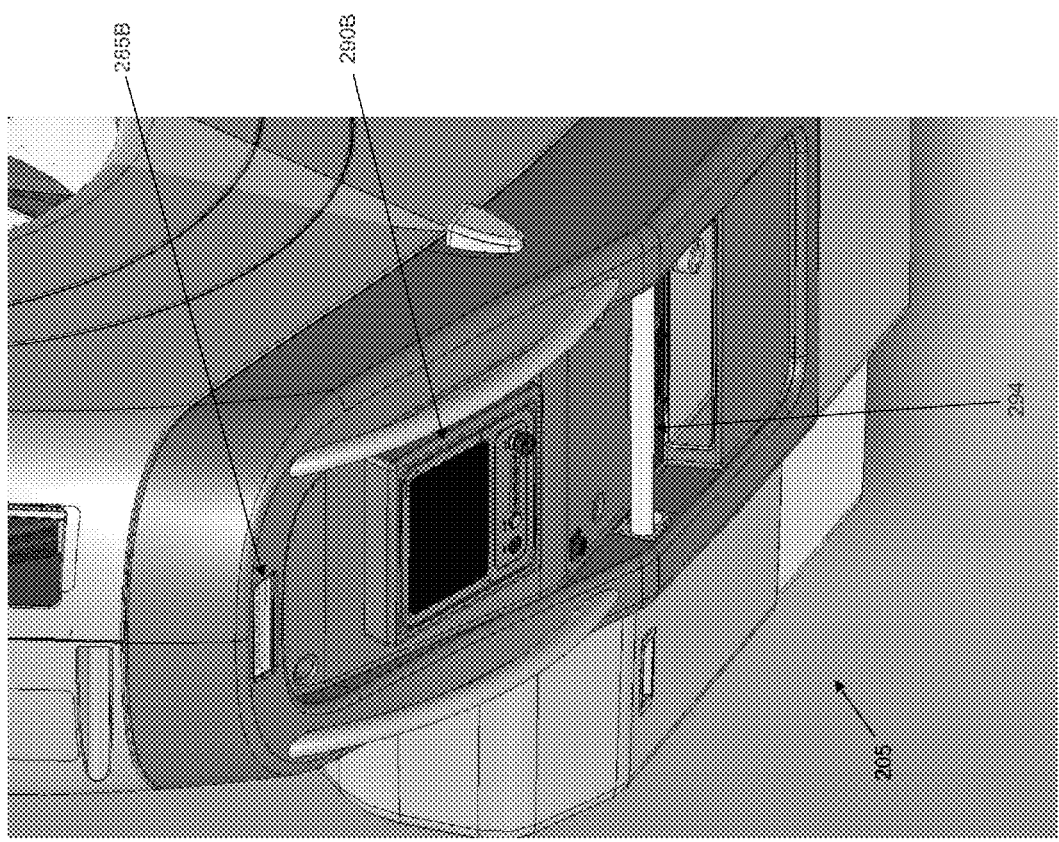
Figure 26:
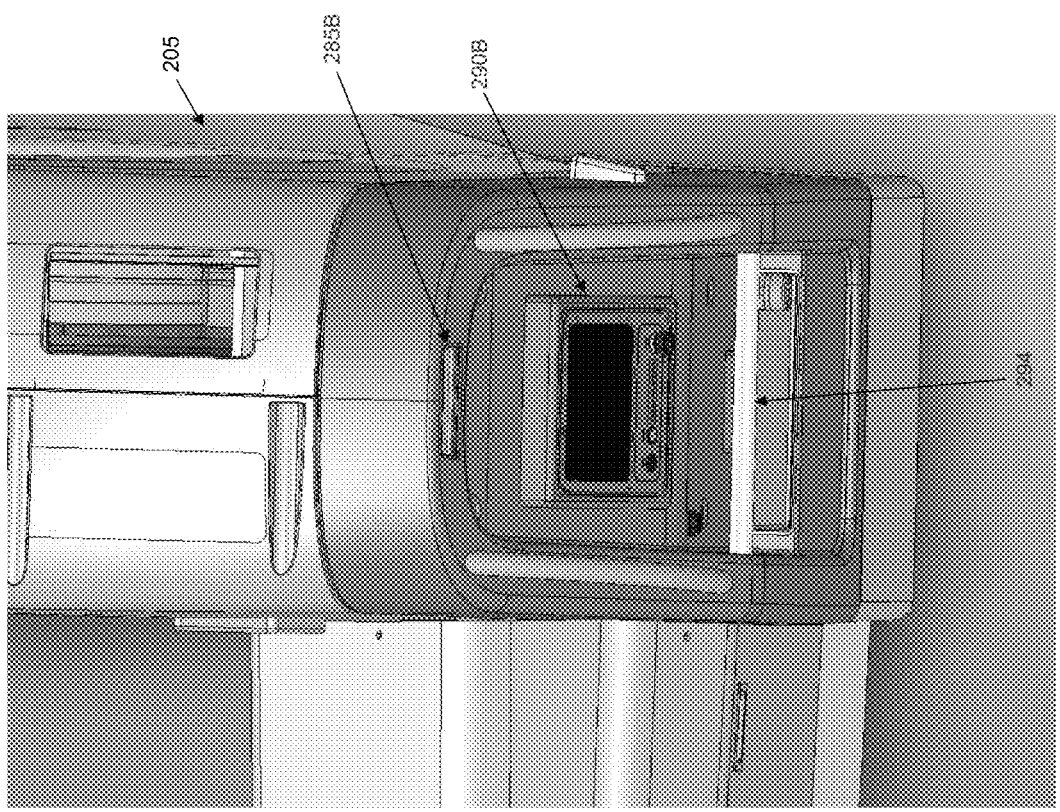

More particularly, and looking now at FIGS. 8-11, there is shown a BodyTom™ CT machine 205 formed in accordance with the present invention. In one preferred form of the invention, BodyTom™ CT machine 205 is preferably substantially the same as the aforementioned CereTom® CT machine 5, except that (i) BodyTom™ CT machine 205 is scaled up in size so that central opening 220 of BodyTom™ CT machine 205 can receive the full body of a patient (and horizontally-extending surgical platform 105), and (ii) a bottom notch 280 is provided in skirt 275 of BodyTom™ CT machine 205. Bottom notch 280 is sized, relative to horizontally-extending base 110 of patient support 100, so that BodyTom™ CT machine 205 can encompass the patient's torso (and surgical platform 105) in its central opening 220 during scanning, with horizontally-extending base 110 being received in bottom notch 280 of BodyTom™ CT machine 205. In other words, bottom notch 280 has a width 282 (FIG. 11) which is wider that the width 127 (FIG. 5) of horizontally-extending base 110, and bottom notch 280 has a height 283 (FIG. 11) which is taller than the height 128 (FIG. 5) of horizontally-extending base 110. By way of example but not limitation, in one preferred form of the present invention, bottom notch 280 has a width 282 of approximately 34.1 inches and a height 283 of approximately 6.8 inches. Thus, where the lowest point of skirt 275 sits approximately 2.2 inches above the surface of the floor when BodyTom™ CT machine 205 is supported on its centipede belt drives, the top of bottom notch 280 sits approximately 9.0 inches from the surface of the floor. It will, of course, also be appreciated that the ground-engaging elements of the machine's transport assembly (e.g., the various casters and centipede belt drives previously discussed) are located outboard of bottom notch 280, in order to keep bottom notch 280 clear to receive the base of a patient support.

See FIGS. 12-15, which show BodyTom™ CT machine 205 in various positions relative to patient support 110 and the patient. In particular, note how BodyTom™ CT machine 205 has its central opening 220 and its bottom notch 280 configured so that BodyTom™ CT machine 205 can encompass the patient's torso (and surgical platform 105) in central opening 220 during scanning, with horizontally-extending base 110 being received in bottom notch 280 of BodyTom™ CT machine 205.

If desired, casters 62 of gross movement mechanism 55 can be replaced with an alternative gross movement mechanism, e.g., wheels, rolling balls, etc. Furthermore, if desired, centipede belt drives 63 of fine movement mechanism 60 can be replaced with an alternative floor crawler mechanism, e.g., a tracked floor crawler mechanism, a wheeled floor crawler mechanism, etc.

Also, if desired, a video camera/video screen system can be provided on BodyTom™ CT machine 205 in order to assist the operator in safely navigating around obstacles which might otherwise be obstructed from the view of the operator when transporting and/or positioning the machine. This feature can be particularly important in view of the increased size of BodyTom™ CT machine 205. In one preferred form of the invention, video cameras and video screens are provided on each end of BodyTom™ CT machine 205, so that the operator can maneuver the machine from either end. By way of example but not limitation, video cameras 285A, 285B and video screens 290A, 290B may be provided, with the operator viewing the output of video camera 285A on video screen 290B or the output of video camera 285B on video screen 290A. Thus, the operator can maneuver the BodyTom™ CT machine 205 from the trailing end of the machine while still seeing whatever may be in front of the leading end of the machine. In one preferred form of the invention, video screens 290A, 290B are also used to provide output to the operator when BodyTom™ CT machine 205 is being used in scanning mode, set-up mode, etc.

Furthermore, if desired, batteries 70 can be Lithium-Ion batteries.

BodyTom™ CT Machine with Motorized Drive

In one preferred form of the present invention, the BodyTom™ CT machine 205 comprises a motorized drive.

Figure 1:
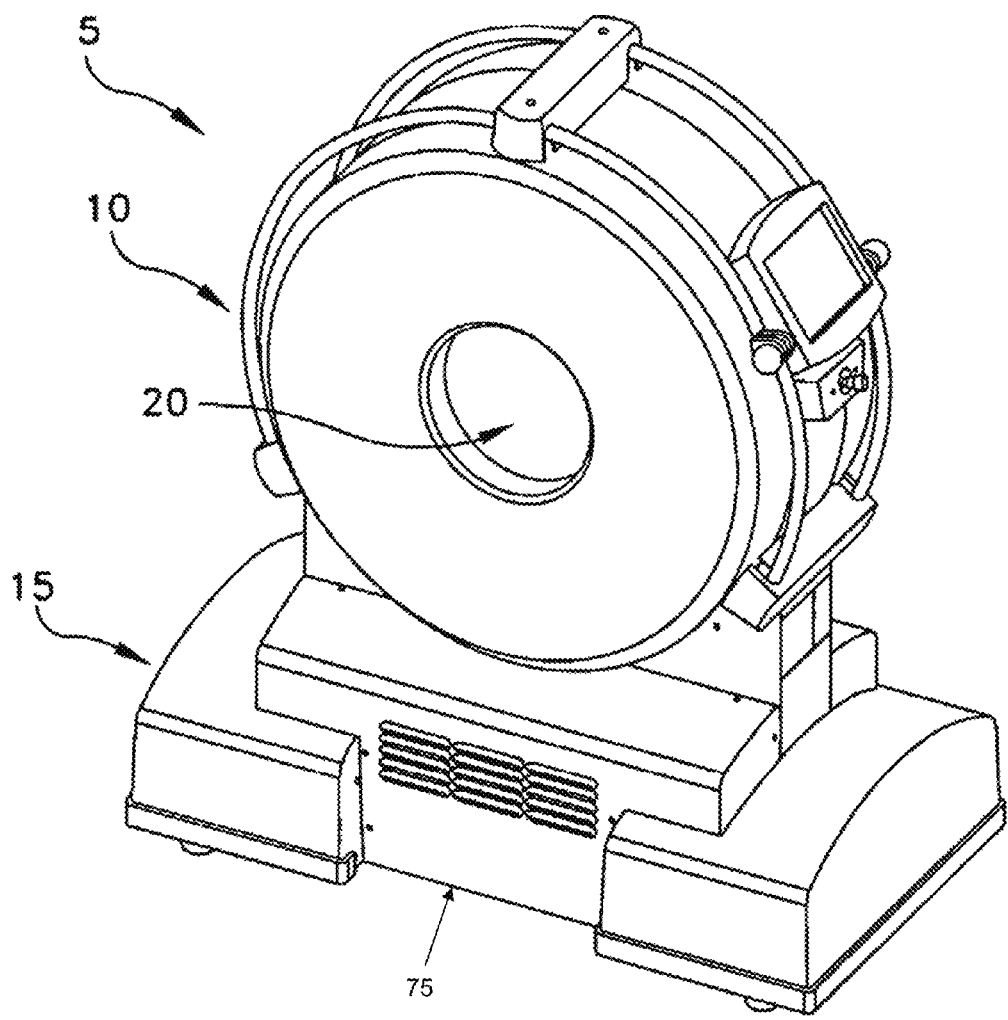
FIGS. 1-4 are schematic views showing a CereTom® CT machine of the sort made by Neurologica Corp. of Danvers, Mass.
Figure 2:
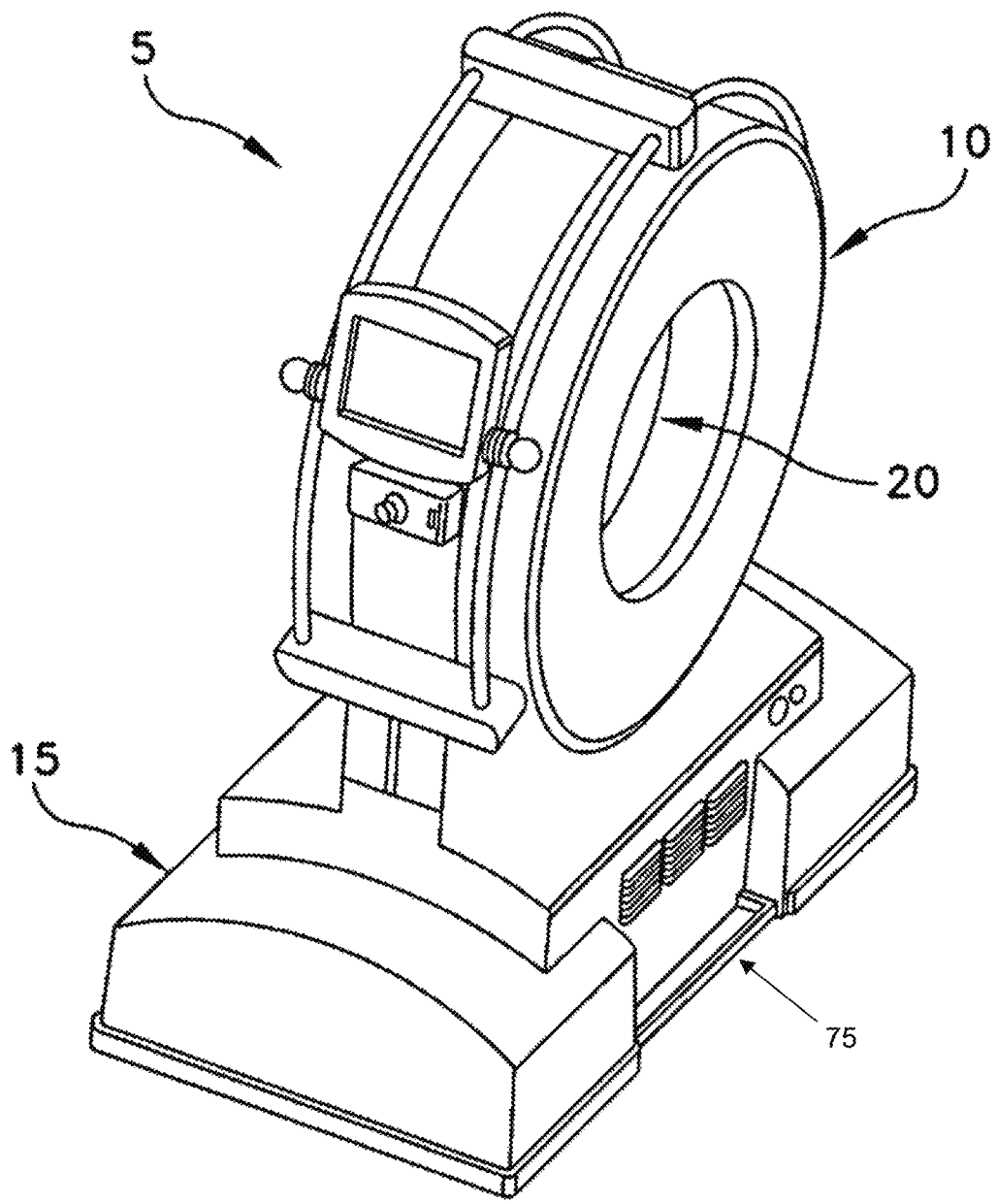
Figure 3:
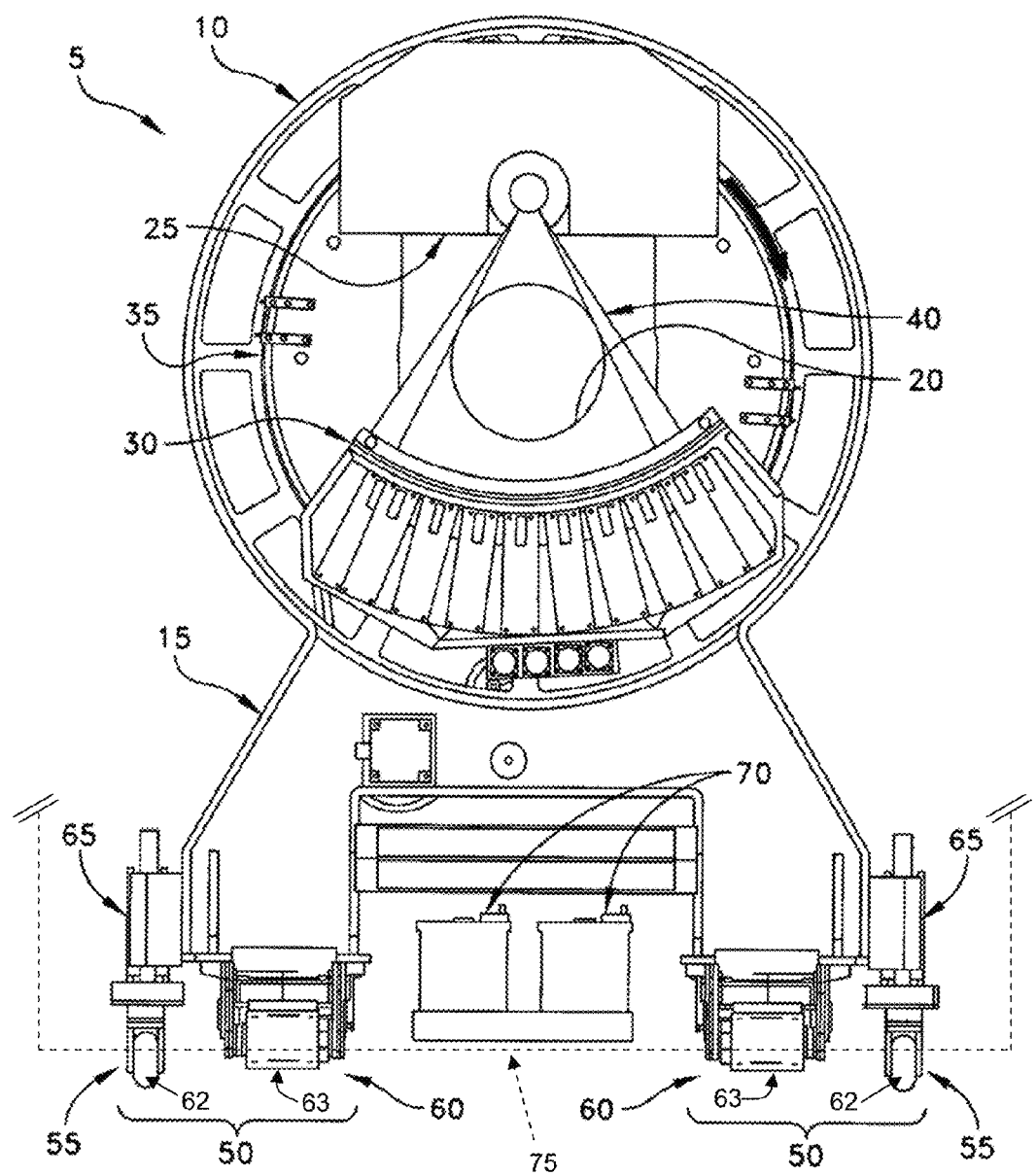
Figure 4:
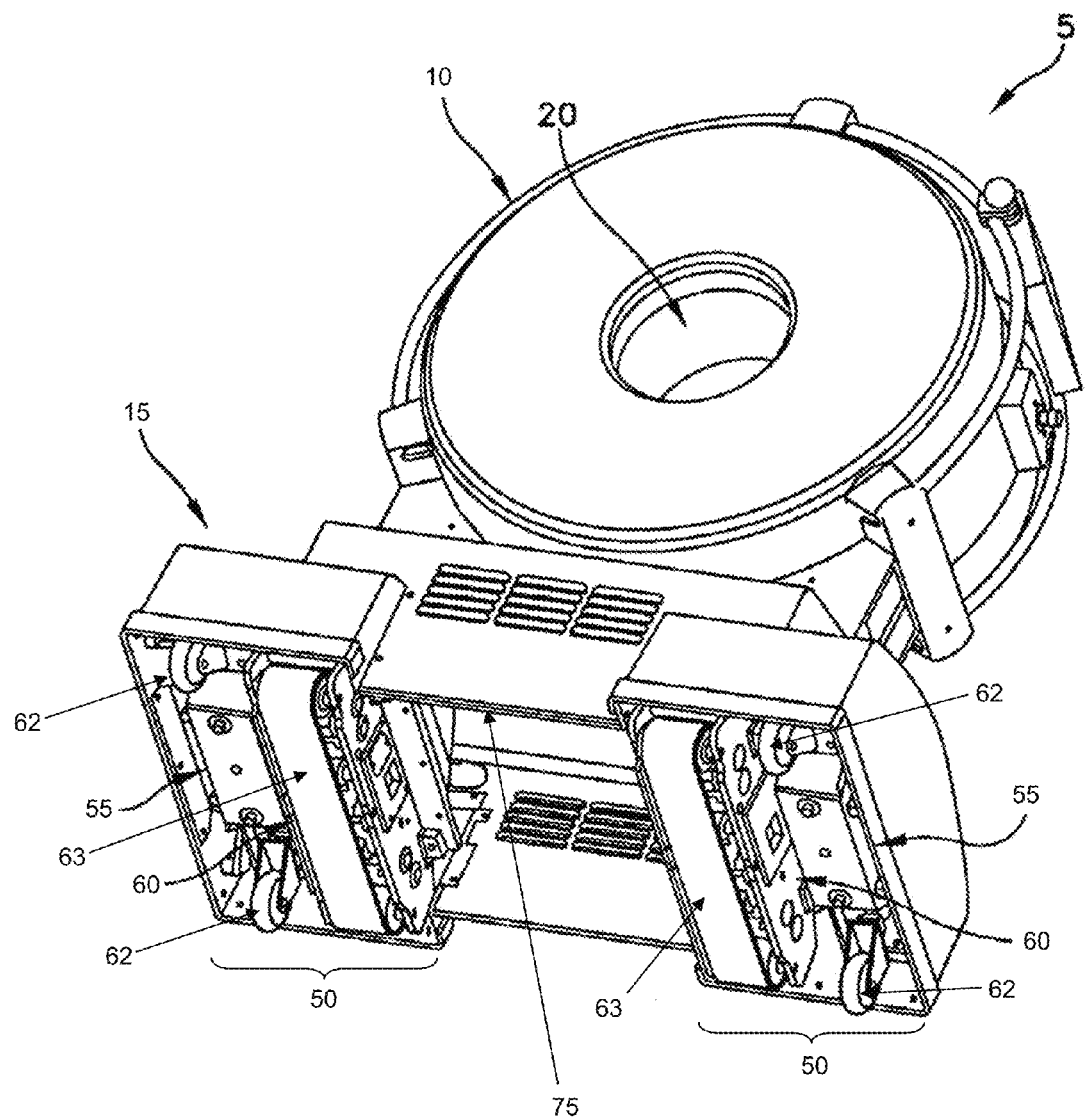

More particularly, in this form of the invention, and looking now at FIGS. 16-26, the BodyTom™ CT machine 205 is preferably substantially the same as the aforementioned CereTom® CT machine 5, except that the casters 62 of gross movement mechanism 55 (FIG. 3) are replaced by a pair of drive wheels 291 (FIGS. 16 and 17) and a pair of casters 292, and means are provided for permitting a user to selectively power each of the drive wheels 291 forwardly or rearwardly so as to steerably drive the BodyTom™ CT machine 205. Furthermore, the centipede belt drives 63 of fine movement mechanism 60 (FIG. 3) may comprise a pair of parallel drive belts 60A, 60B disposed in side-by-side relation (FIG. 17), so that a pair of parallel drive belts 60A, 60B are disposed on each side of the machine (FIG. 17), rather than a single drive belt 60 being disposed on each side of the machine (FIG. 3).

More particularly, and looking now at FIGS. 18-21, a drive bar 293 is provided to control the application of power to each of the drive wheels 291. Preferably, drive bar 293 is configured so that when the right side 293A of drive bar 293 is pressed forwardly (i.e., toward the body of the BodyTom™ CT machine 205), drive wheel 291A is caused to rotate forwardly, and when the right side 293A of drive bar 293 is pulled rearwardly (i.e., away from the body of the BodyTom™ CT machine 205), drive wheel 291A is caused to rotate rearwardly. Correspondingly, when the left side 293B of drive bar 293 is pressed forwardly (i.e., toward the body of the BodyTom™ CT machine 205), drive wheel 291B is caused to rotate forwardly, and when the left side 293B of drive bar 293 is pulled rearwardly (i.e., away from the body of the BodyTom™ CT machine 205), drive wheel 291B is caused to rotate rearwardly. Significantly, the right side 293A of drive bar 293, and the left side 293B of drive bar 293, may be moved (i) forwardly together, in which case drive wheels 291A, 291B move forwardly together, (ii) rearwardly together, in which case drive wheels 291A, 291B move rearwardly together, or (iii) in opposite directions, in which case drive wheels 291A, 291B move oppositely to one another.

Preferably, the amount of power applied to the drive wheels 291 is proportional to the amount of force applied to each end of drive bar 293, and power to drive wheels 291 is terminated if no force is being applied to drive bar 293.

Thus, it will be seen that, to move the BodyTom™ CT machine 205 forwardly, the right side 293A of drive bar 293, and the left side 293B of drive bar 293, are both pushed forwardly (FIG. 22A); to move the BodyTom™ CT machine 205 rearwardly, the right side 293A of drive bar 293, and the left side 293B of drive bar 293, are both pulled rearwardly (FIG. 22B); to turn the BodyTom™ CT machine 205 to the left, the right side 293A of drive bar 293 may be pressed forwardly and the left side 293B of drive bar 293 may be pulled rearwardly (FIG. 22C); and to turn the BodyTom™ CT machine 205 to the right, the left side 293B of drive bar 293 may be pressed forwardly and the right side 293A may be pulled rearwardly (FIG. 22D).

If desired, a counterpart drive bar 294 may be provided on the opposite end of the BodyTom™ CT machine 205 (FIGS. 23-26), whereby to allow the machine to be "driven" from either end of the machine.

Preferably, BodyTom™ CT machine 205 includes the aforementioned video cameras 285A, 285B and the aforementioned video screens 290A, 290B (FIGS. 18-21 and 23-26). BodyTom™ CT machine 205 is preferably configured so that when the machine is being operated in scanning mode, video screens 290A, 290B provide information and/or images to the operator of the machine. BodyTom™ CT machine 205 is preferably also configured so when BodyTom™ CT machine 205 is being driven by drive wheels 291, video camera 285A is automatically activated and its acquired image displayed on display screen 290B, and video camera 285B is automatically activated and its acquired image displayed on display screen 290A. As a result, the operator is able to see where BodyTom™ CT machine 205 is going when it is being driven via drive bar 287 or drive bar 294. To this end, display screens 290A, 290B are preferably located at about eye level to an operator who has their hands placed on drive bar 287 or drive bar 294.

As a result of the foregoing constructions, BodyTom™ CT machine 205 can be easily and safely moved in any direction, since it allows the operator to drive the machine from either end of the machine via drive bars 287, 294, and see what is immediately ahead of the leading end of the machine via video cameras 285A, 285B and display screens 290A, 290B.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines used to scan inanimate objects which are to be supported on an object support which needs to be encompassed by the CT machine (e.g., in the center opening of the CT machine and the bottom notch of the CT machine). Furthermore, the present invention may be used with non-CT-type scanning systems. Thus, for example, the present invention may be used in conjunction with SPECT machines, MRI machines, PET machines, X-ray machines, etc., i.e., wherever the scanning machine must accommodate portions of a support within the scanning machine during scanning.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. Apparatus for imaging an object, the apparatus comprising:
    a CT machine configured to move on a surface, the CT machine comprising a leading end and a trailing end, wherein the CT machine comprises a camera and a viewing screen, wherein the output of the camera is displayed on the viewing screen, and further wherein the camera is disposed on the leading end of the CT machine so as to capture an image of the space ahead of the leading end of the CT machine during movement of the CT machine across the surface;
    wherein the CT machine is further configured to image the object while the object is supported on a support, the support comprising a base for positioning on a surface, wherein the object and the support are stationary relative to the surface, and further wherein the CT machine is adapted to move relative to the surface, and hence relative to the object and to the support, during imaging;

the CT machine comprising a housing having a bottom notch sized to accommodate the base of the support, whereby to allow the base of the support to extend into the housing during imaging.

2. Apparatus according to claim 1 wherein the viewing screen is disposed on the trailing end of the CT machine.

3. Apparatus according to claim 1 wherein the CT machine comprises a second camera and a second viewing screen, wherein the output of the camera is displayed on the second viewing screen and the output of the second camera is displayed on the viewing screen, and further wherein the camera and the second viewing screen are disposed on the leading end of the CT machine and the second camera and the viewing screen are disposed on the trailing end of the CT machine.

4. Apparatus according to claim 1 wherein the apparatus is configured to image anatomy.

5. Apparatus according to claim 1 wherein the apparatus is configured to image an inanimate object.

6. Apparatus according to claim 1 wherein the apparatus comprises a gross movement mechanism for moving the CT machine across the surface when not imaging, and further wherein the gross movement mechanism comprises at least one wheel.

7. Apparatus according to claim 1 wherein the apparatus comprises a gross movement mechanism for moving the CT machine across the surface when not imaging, and further wherein the gross movement mechanism is powered by a motor.

8. Apparatus according to claim 1 wherein the apparatus comprises a fine movement mechanism for moving the CT machine precisely, relative to the object, during imaging, and further wherein the fine movement mechanism comprises at least one centipede belt drive.

9. Apparatus according to claim 8 wherein the fine movement mechanism comprises a pair of centipede belt drives.

10. Apparatus according to claim 1 wherein the surface comprises the floor of a room.

11. Apparatus according to claim 1 wherein the surface comprises the floor of a vehicle.

12. Apparatus according to claim 1 wherein the support comprises a horizontally-extending base, a vertically-extending riser and a horizontally-extending platform, and further wherein the horizontally-extending platform is cantilevered over at least a portion of the horizontally-extending base.

13. Apparatus according to claim 12 wherein the horizontally-extending platform is sized to receive the body of a patient.

14. Apparatus according to claim 1 wherein the apparatus comprises a fine movement mechanism for moving the CT machine precisely, relative to the object, during imaging, and wherein the fine movement mechanism comprises a pair of centipede belt drives, and further wherein one centipede belt drive is disposed on either side of the bottom notch.

15. A method for moving an imaging device on a surface, the method comprising:

providing a CT machine comprising a leading end and a trailing end, wherein the CT machine comprises a camera and a viewing screen, wherein the output of the camera is displayed on the viewing screen, and further wherein the camera is disposed on the leading end of the CT machine so as to capture an image of the space ahead of the leading end of the CT machine;

wherein the CT machine is further configured to image the object while the object is supported on a support, the support comprising a base for positioning on a surface, wherein the object and the support are stationary relative to the surface, and further wherein the CT machine is adapted to move relative to the surface, and hence relative to the object and to the support, during imaging;

the CT machine comprising a housing having a bottom notch sized to accommodate the base of the support, whereby to allow the base of the support to extend into the housing during imaging; and moving the CT machine across the surface while capturing an image of the space ahead of the leading end of the CT machine.

16. A method according to claim 15 wherein the surface comprises the floor of a room.

17. A method according to claim 15 wherein the surface comprises the floor of a vehicle.

18. A method according to claim 15 wherein the support comprises a horizontally-extending base, a vertically-extending riser and a horizontally-extending platform, and further wherein the horizontally-extending platform is cantilevered over at least a portion of the horizontally-extending base.

19. A method according to claim 18 wherein the horizontally-extending platform is sized to receive the body of a patient.

20. A method according to claim 15 wherein the apparatus comprises a fine movement mechanism for moving the CT machine precisely, relative to the object, during imaging, and wherein the fine movement mechanism comprises a pair of centipede belt drives, and further wherein one centipede belt drive is disposed on either side of the bottom notch.

21. A method according to claim 15 wherein the viewing screen is disposed on the trailing end of the CT machine.

22. A method according to claim 15 wherein the CT machine comprises a second camera and a second viewing screen, wherein the output of the camera is displayed on the second viewing screen and the output of the second camera is displayed on the viewing screen, and further wherein the camera and the second viewing screen are disposed on the leading end of the CT machine and the second camera and the viewing screen are disposed on the trailing end of the CT machine.

23. A method according to claim 15 wherein the CT machine is configured to image anatomy.

24. A method according to claim 15 wherein the CT machine is configured to image an inanimate object.

25. A method according to claim 15 wherein the CT machine comprises a gross movement mechanism for moving the CT machine across the surface when not imaging, and further wherein the gross movement mechanism comprises at least one wheel.

26. A method according to claim 15 wherein the CT machine comprises a gross movement mechanism for moving the CT machine across the surface when not imaging, and further wherein the gross movement mechanism is powered by a motor.

27. A method according to claim 15 wherein the CT machine comprises a fine movement mechanism for moving the CT machine precisely, relative to the object, during imaging, and further wherein the fine movement mechanism comprises at least one centipede belt drive.

28. A method according to claim 27 wherein the fine movement mechanism comprises a pair of centipede belt drives.

\* \* \* \* \*